(12) United States Patent
Chae et al.

(10) Patent No.: US 10,988,447 B2
(45) Date of Patent: Apr. 27, 2021

(54) BIPYRIDINE DERIVATIVES AND THEIR USES FOR ORGANIC LIGHT EMITTING DIODES

(71) Applicant: Samsung Electronics Co., Ltd., Suwon-si (KR)

(72) Inventors: Hyun Sik Chae, Cambridge, MA (US); Kyungdoc Kim, Suwon-si (KR); Sae Youn Lee, Suwon-si (KR); Soonok Jeon, Suwon-si (KR); Hiroshi Miyazaki, Suwon-si (KR); Masaki Numata, Suwon-si (KR); Youngmin Nam, Suwon-si (KR); Tae-Rae Kim, Suwon-si (KR); In Koo Kim, Suwon-si (KR); Won-Joon Son, Suwon-si (KR); Won Seok Oh, Suwon-si (KR); Younsuk Choi, Suwon-si (KR); Sunghan Kim, Suwon-si (KR); Jeong-Ju Cho, Cambridge, MA (US)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 240 days.

(21) Appl. No.: 15/632,518

(22) Filed: Jun. 26, 2017

(65) Prior Publication Data
US 2018/0002287 A1    Jan. 4, 2018

Related U.S. Application Data

(60) Provisional application No. 62/357,105, filed on Jun. 30, 2016.

(51) Int. Cl.
*C07D 213/22* (2006.01)
*C09K 11/06* (2006.01)
(Continued)

(52) U.S. Cl.
CPC ............ *C07D 213/22* (2013.01); *C09K 11/06* (2013.01); *H01L 51/0054* (2013.01);
(Continued)

(58) Field of Classification Search
None
See application file for complete search history.

(56) References Cited

U.S. PATENT DOCUMENTS 8,168,307 B2    5/2012    Iida et al.
8,435,679 B2    5/2013    Lamanna et al.
(Continued)

FOREIGN PATENT DOCUMENTS

KR    20130117534 A    10/2013
WO    2010090925 A1    8/2010
(Continued)

OTHER PUBLICATIONS

Notice of Allowance dated Jul. 19, 2017; U.S. Appl. No. 14/667,617, filed Mar. 24, 2015 (9 pages).
(Continued)

*Primary Examiner* — Jay Yang
(74) *Attorney, Agent, or Firm* — Cantor Colburn LLP

(57) ABSTRACT

A condensed cyclic compound represented by Formula 1:

$$Ar^1\text{-}(L_1)_{a1}\text{-}B\text{-}(L_2)_{a2}\text{-}Ar^2 \quad \text{Formula 1}$$

wherein, in Formula 1, groups and variables are the same as described in the specification.

19 Claims, 7 Drawing Sheets

(51) Int. Cl.
  *H01L 51/00* (2006.01)
  *H01L 51/50* (2006.01)
(52) U.S. Cl.
  CPC ...... *H01L 51/0067* (2013.01); *H01L 51/0071* (2013.01); *H01L 51/0072* (2013.01); *C09K 2211/1007* (2013.01); *C09K 2211/1011* (2013.01); *C09K 2211/1029* (2013.01); *C09K 2211/1033* (2013.01); *C09K 2211/1037* (2013.01); *C09K 2211/1044* (2013.01); *C09K 2211/1092* (2013.01); *C09K 2211/185* (2013.01); *H01L 51/5012* (2013.01); *H01L 51/5016* (2013.01)

(56) References Cited

U.S. PATENT DOCUMENTS

| | | |
|---|---|---|
| 8,643,268 B2 | 2/2014 | Ogiwara et al. |
| 9,219,242 B2 | 12/2015 | Ogiwara et al. |
| 9,276,228 B2 | 3/2016 | Seo et al. |
| 9,328,097 B2 | 5/2016 | Xu et al. |
| 2010/0187984 A1 | 7/2010 | Lin et al. |
| 2010/0327265 A1 | 12/2010 | Kimura et al. |
| 2012/0153272 A1* | 6/2012 | Fukuzaki .............. C07D 487/04 257/40 |
| 2015/0270494 A1 | 9/2015 | Xu et al. |
| 2015/0280158 A1 | 10/2015 | Ogiwara et al. |
| 2016/0075718 A1* | 3/2016 | Mitsumori ........... C07D 495/04 257/40 |
| 2016/0093813 A1 | 3/2016 | Stoessel et al. |
| 2016/0168162 A1 | 6/2016 | Chae et al. |
| 2016/0181529 A1 | 6/2016 | Tsai et al. |
| 2016/0181545 A1 | 6/2016 | Stoessel et al. |

FOREIGN PATENT DOCUMENTS

| | | |
|---|---|---|
| WO | WO-2011/025018 A1 * | 3/2011 |
| WO | 2015108049 A1 | 7/2015 |
| WO | 2016116517 A1 | 7/2016 |

OTHER PUBLICATIONS

Restriction Election Requirement dated Mar. 28, 2017; U.S. Appl. No. 14/667,617, filed Mar. 24, 2015 (6 pages).

* cited by examiner

BIPYRIDINE DERIVATIVES AND THEIR USES FOR ORGANIC LIGHT EMITTING DIODES

CROSS-REFERENCE TO RELATED APPLICATION

This application claims priority to U.S. Provisional Patent Application No. 62/357,105 filed on Jun. 30, 2016, in the United States Patent and Trademark Office, and all the benefits accruing therefrom under 35 U.S.C. § 119, the content of which is incorporated herein in its entirety by reference.

BACKGROUND

1. Field

The present disclosure relates to a condensed cyclic compound and an organic light-emitting device including the same.

2. Description of the Related Art

Organic light-emitting devices (OLEDs) are self-emission devices that have wide viewing angles, high contrast ratios, and short response times. In addition, OLEDs exhibit excellent brightness, driving voltage, and response speed characteristics, and produce full-color images, compared to electronic devices of the related art.

In an example, an organic light-emitting device includes an anode, a cathode, and an organic layer that is disposed between the anode and the cathode and includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, are recombined in the emission layer to produce excitons. These excitons change from an excited state to a ground state, thereby generating light.

Various types of organic light emitting devices are known. However, there still remains a need in OLEDs having low driving voltage, high efficiency, high brightness, and long lifespan.

SUMMARY

Provided are novel condensed cyclic compounds and organic light-emitting devices including the same.

Additional aspects will be set forth in part in the description which follows and, in part, will be apparent from the description, or may be learned by practice of the presented exemplary embodiments.

An embodiment provides a condensed cyclic compound represented by Formula 1:

Formula 1

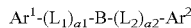

wherein, in Formula 1,
B is a group represented by Formula 2:

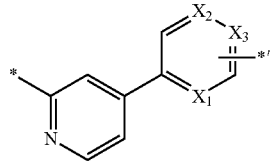

Formula 2 wherein, in Formula 2,
$X_1$ is N or CH, $X_2$ is N or CH, and $X_3$ is N or CH;
$L_1$ and $L_2$ are each independently selected from a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, wherein at least one of substituents of the substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_2$-$C_{60}$ heteroaryloxy group, substituted $C_2$-$C_{60}$ heteroarylthio group, and substituted $C_3$-$C_{60}$ heteroarylalkyl group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, and —Si($Q_1$)($Q_2$)($Q_3$), wherein $Q_1$ to $Q_3$ are each independently selected from a hydrogen, a $C_1$-$C_{60}$ alkyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, and a $C_1$-$C_{60}$ heteroaryl group;
* represents a point of connection to $Ar^1$;
*' represents a point of connection to $Ar^2$;
a1 and a2 are each independently an integer selected from 0 to 5, provided that
when a1 is 2 or greater, two or more groups $L_1$ are identical to or different from each other, and
when a2 is 2 or greater, two or more groups $L_2$ are identical to or different from each other;
$Ar^1$ and $Ar^2$ are each independently a group represented by one of Formulae 3A to 3F

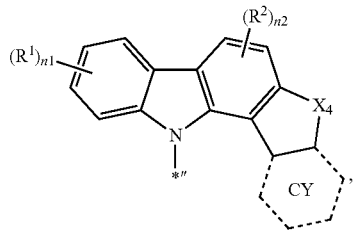

Formula 3A

-continued

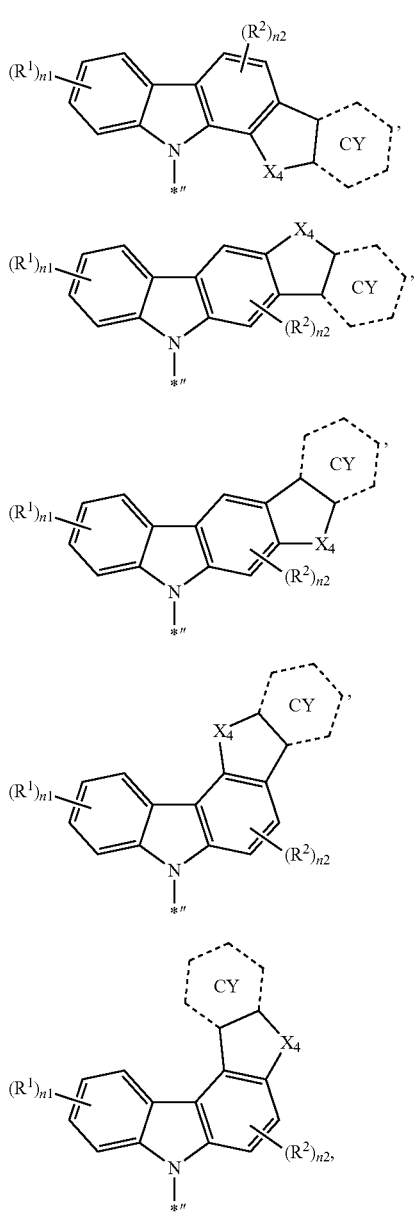

Formula 3B

Formula 3C

Formula 3D

Formula 3E

Formula 3F wherein, in Formulae 3A to 3F,

CY is a substituted or unsubstituted $C_6$-$C_{60}$ aryl ring or a substituted or unsubstituted $C_1$-$C_{60}$ heteroaryl ring, $X_4$ is O, S, Se, $N(R_3)$, $P(=O)(R_4)$, $C(R_5)(R_6)$, or $Si(R_7)(R_8)$, n1 is 0, 1, 2, or 4, n2 is 0 or 1, $R^1$, $R^2$, and $R^5$ to $R^8$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_1$-$C_{60}$ heterocycloalkyl group, a substituted or unsubstituted $C_3$-$C_{60}$ cycloalkenyl group, a substituted or unsubstituted $C_1$-$C_{60}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, and —$Si(Q_4)(Q_5)(Q_6)$, wherein $Q_4$ to $Q_6$ are each independently selected from a hydrogen, a $C_1$-$C_{60}$ alkyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, and a $C_1$-$C_{60}$ heteroaryl group, $R^3$ and $R^4$ is a substituted or unsubstituted $C_6$-$C_{60}$ aryl group or a substituted or unsubstituted $C_1$-$C_{60}$ heteroaryl group, wherein at least one of substituents of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{60}$ heterocycloalkyl group, substituted $C_3$-$C_{60}$ cycloalkenyl group, substituted $C_1$-$C_{60}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_2$-$C_{60}$ heteroaryloxy group, substituted $C_2$-$C_{60}$ heteroarylthio group, and substituted $C_3$-$C_{60}$ heteroarylalkyl group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, and —$Si(Q_7)(Q_8)(Q_9)$, wherein $Q_7$ to $Q_9$ are each independently selected from a hydrogen, a $C_1$-$C_{60}$ alkyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, and a $C_1$-$C_{60}$ heteroaryl group, and

*" represents a point of connection to B.

Another embodiment provides an organic light-emitting device includes:

a first electrode, a second electrode, and an organic layer disposed between the first electrode and the second electrode, wherein the organic layer including an emission layer and at least one of the condensed cyclic compounds represented by Formula 1 described above.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
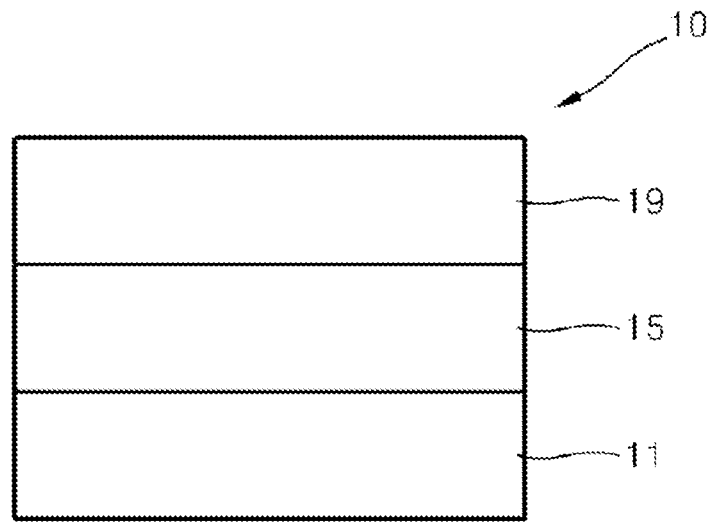
FIG. 1 shows a schematic cross-sectional view of an organic light-emitting device according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Provided herein are novel condensed cyclic compounds and organic light-emitting devices including the condensed cyclic compounds.

In an embodiment, the condensed cyclic compound may be represented by Formula 1:

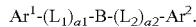  Formula 1

In Formula 1,

B may be a group represented by Formula 2:

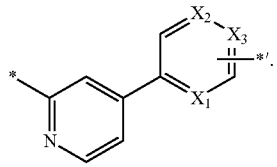  Formula 2

In Formula 2, $X_1$ may be N or CH, $X_2$ may be N or CH, and $X_3$ may be N or CH;

$L_1$ and $L_2$ may be each independently selected from a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, wherein at least one of substituents of the substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_2$-$C_{60}$ heteroaryloxy group, substituted $C_2$-$C_{60}$ heteroarylthio group, and substituted $C_3$-$C_{60}$ heteroarylalkyl group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, and —Si($Q_1$)($Q_2$)($Q_3$), wherein $Q_1$ to $Q_3$ are each independently selected from a hydrogen, a $C_1$-$C_{60}$ alkyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, and a $C_1$-$C_{60}$ heteroaryl group;

\* may represent a point of connection to $Ar^1$;

\*' may represent a point of connection to $Ar^2$;

a1 and a2 may be each independently an integer selected from 0 to 5, provided that when a1 is 2 or greater, two or more groups $L_1$ may be identical to or different from each other, and when a2 is 2 or greater, two or more groups $L_2$ may be identical to or different from each other.

In Formula 2, $Ar^1$ and $Ar^2$ may be each independently a group represented by one of Formulae 3A to 3F

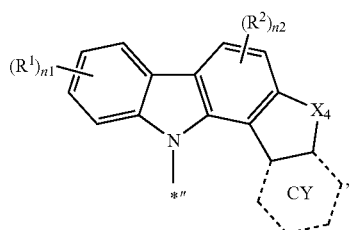  Formula 3A

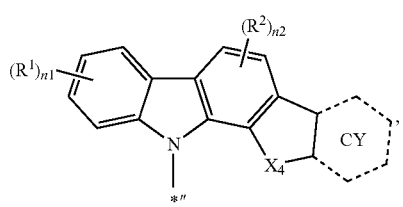  Formula 3B

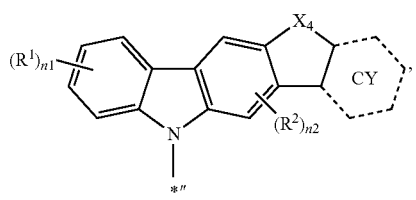  Formula 3C

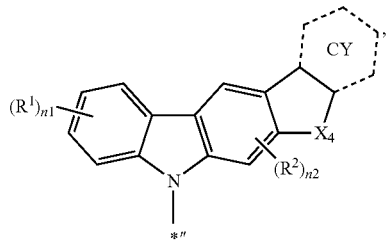  Formula 3D

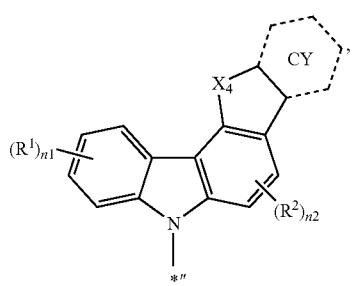  Formula 3E

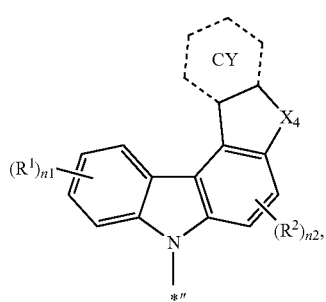  Formula 3F

In Formulae 3A to 3F,

CY may be a substituted or unsubstituted $C_6$-$C_{60}$ aryl ring or a substituted or unsubstituted $C_1$-$C_{60}$ heteroaryl ring, $X_4$ may be O, S, Se, $N(R_3)$, $P(=O)(R_4)$, $C(R_5)(R_6)$, or $Si(R_7)(R_8)$, n1 may be 0, 1, 2, or 4, n2 may be 0 or 1, $R^1$, $R^2$, and $R^5$ to $R^8$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_1$-$C_{60}$ heterocycloalkyl group, a substituted or unsubstituted $C_3$-$C_{60}$ cycloalkenyl group, a substituted or unsubstituted $C_1$-$C_{60}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, and —$Si(Q_4)(Q_5)(Q_6)$, wherein $Q_4$ to $Q_6$ are each independently selected from a hydrogen, a $C_1$-$C_{60}$ alkyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, and a $C_1$-$C_{60}$ heteroaryl group, $R^3$ and $R^4$ may be a substituted or unsubstituted $C_6$-$C_{60}$ aryl group or a substituted or unsubstituted $C_1$-$C_{60}$ heteroaryl group, wherein at least one of substituents of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{60}$ heterocycloalkyl group, substituted $C_3$-$C_{60}$ cycloalkenyl group, substituted $C_1$-$C_{60}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_2$-$C_{60}$ heteroaryloxy group, substituted $C_2$-$C_{60}$ heteroarylthio group, and substituted $C_3$-$C_{60}$ heteroarylalkyl group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, and —$Si(Q_7)(Q_8)(Q_9)$, wherein $Q_7$ to $Q_9$ are each independently selected from a hydrogen, a $C_1$-$C_{60}$ alkyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, and a $C_1$-$C_{60}$ heteroaryl group, and

*''' may represent a point of connection to B.

In some embodiments, in Formula 2, $X_1$ may be N, $X_2$ may be CH, and $X_3$ may be CH;

$X_1$ may be CH, $X_2$ may be N, and $X_3$ may be CH; or $X_1$ may be CH, $X_2$ may be CH, and $X_3$ may be N.

In some embodiments, in Formula 1, $L_1$ and $L_2$ may be each independently selected from a phenylene group, a pyridinylene group, a pyrimidinylene group, a pyrazinylene group, a pyridazinylene group, a triazinylene group, a dibenzofuranylene group, and a dibenzothiophenylene group; and a phenylene group, a pyridinylene group, a pyrimidinylene group, a pyrazinylene group, a pyridazinylene group, a triazinylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —$Si(Q_{10})(Q_{11})(Q_{12})$, wherein $Q_{10}$ to $Q_{12}$ are each independently selected from a hydrogen, a $C_1$-$C_{60}$ alkyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, and a $C_1$-$C_{60}$ heteroaryl group.

In some embodiments, in Formula 1, $L_1$ and $L_2$ are each independently selected from a phenylene group, a pyridinylene group, a pyrimidinylene group, and a triazinylene group; and a phenylene group, a pyridinylene group, a pyrimidinylene group, and a triazinylene group, each substituted with at least one selected from a deuterium, a methyl group, an ethyl group, an n-propyl group, an isopropyl group, an n-butyl group, an isobutyl group, a sec-butyl group, a tert-butyl group, a phenyl group, a pyridinyl group, a pyrimidinyl group, a pyrazinyl group, a pyridazinyl group, a triazinyl group, and —$Si(Q_{10})(Q_{11})(Q_{12})$, wherein $Q_{10}$ to $Q_{12}$ are each independently selected from a hydrogen, a $C_1$-$C_{60}$ alkyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, and a $C_1$-$C_{60}$ heteroaryl group.

In some embodiments, in Formula 1, $L_1$ and $L_2$ may be each independently selected from a phenylene group; and a phenylene group substituted with at least one selected from a deuterium, a methyl group, an ethyl group, an n-propyl group, an isopropyl group, an n-butyl group, an isobutyl group, a sec-butyl group, a tert-butyl group, a phenyl group, a pyridinyl group, a pyrimidinyl group, a pyrazinyl group, a pyridazinyl group, a triazinyl group, and —$Si(Q_{10})(Q_{11})(Q_{12})$, wherein $Q_{10}$ to $Q_{12}$ may be each independently selected from a hydrogen, a $C_1$-$C_{10}$ alkyl group, a $C_1$-$C_{10}$ alkoxy group, and a phenyl group.

In some embodiments, in Formula 1, a1 may be 0 and a2 may be 0. When a1 is 0, $Ar^1$ is directly connected to B. When a2 is 0, $Ar^2$ is directly connected to B.

In some embodiments, in Formulae 3A to 3F, CY may be an unsubstituted $C_6$-$C_{60}$ aryl ring.

In some embodiments, in Formulae 2 and 3A to 3F, $R^1$, $R^2$, and $R^5$ to $R^8$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, a pyrimidinyl group, a pyrazinyl group, a pyridazinyl group, and a triazinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, and an imidazopyridinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, and an imidazopyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, and —Si($Q_{13}$)($Q_{14}$)($Q_{15}$); and —Si($Q_{16}$)($Q_{17}$)($Q_{18}$), wherein $Q_{13}$ to $Q_{15}$ and $Q_{16}$ to $Q_{18}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cinnolinyl group, and a quinazolinyl group.

In some embodiments, in Formulae 2 and 3A to 3F, $R^1$, $R^2$, and $R^5$ to $R^8$ may be each independently selected from a hydrogen, a deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a phenyl group, a naphthyl group, a pyridinyl group, a pyrimidinyl group, a pyrazinyl group, a pyridazinyl group, and a triazinyl group;

a phenyl group, a naphthyl group, a pyridinyl group, a pyrimidinyl group, a pyrazinyl group, a pyridazinyl group, and a triazinyl group, each substituted with at least one selected from a deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si($Q_{13}$)($Q_{14}$)($Q_{15}$); and —Si($Q_{16}$)($Q_{17}$)($Q_{18}$), wherein $Q_{13}$ to $Q_{15}$ and $Q_{16}$ to $Q_{18}$ may be each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group.

In some embodiments, in Formulae 3A to 3F, $R^3$ and $R^4$ may be each a substituted or unsubstituted $C_6$-$C_{60}$ aryl group.

In some embodiments, in Formulae 3A to 3F, $R^3$ and $R^4$ may be each a phenyl group; or a phenyl group substituted with at least one selected from a deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si($Q_{19}$)($Q_{20}$)($Q_{21}$).

In Formulae 3A to 3F, $X_4$ may be O, S, $N(R_3)$, and $C(R_5)(R_6)$, wherein $R_3$ may be a phenyl group and $R_5$ and $R_6$ may be each a methyl group.
In Formula 1, $Ar^1$ and $Ar^2$ may be identical to each other.
In some embodiments, $Ar^1$ and $Ar^2$ may be each independently selected from one of the following groups:
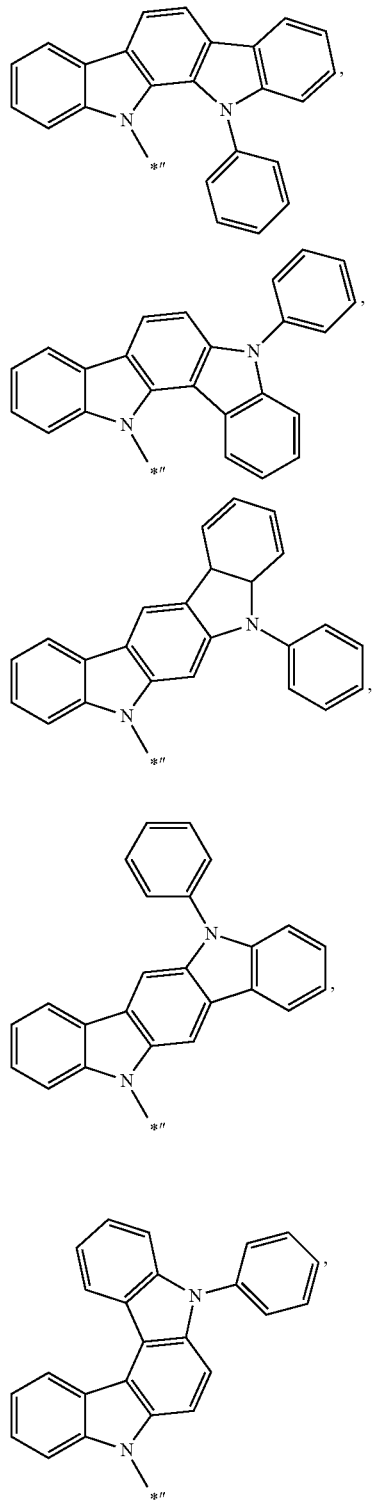
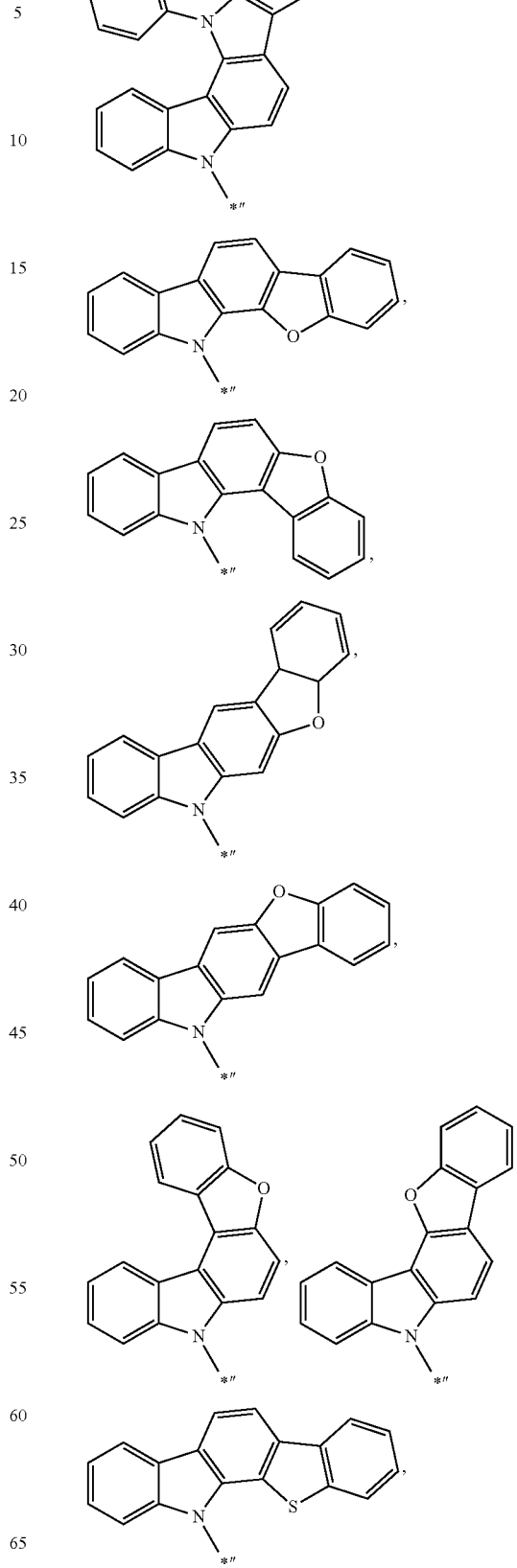

-continued

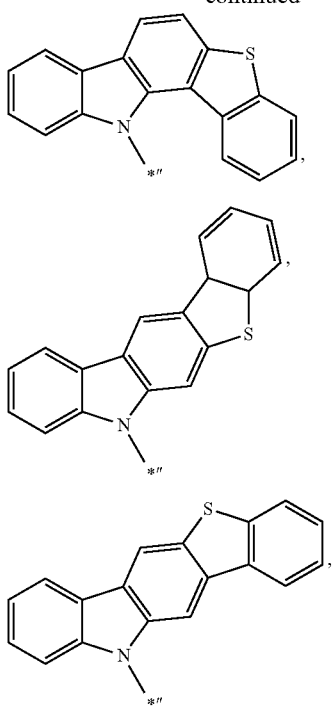

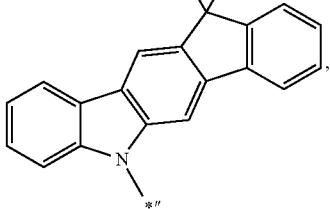

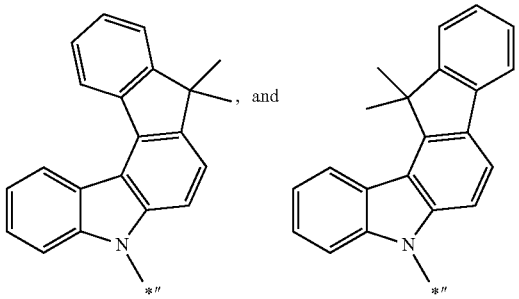

wherein, in the above groups, *″ may represent a point of connection to B.

In some embodiments, Formula 2 may be represented by Formulae 2A and 2B corresponding to asymmetric bipyridine moieties (in which the nitrogen atoms are located asymmetrically across the bipyridine ring system):

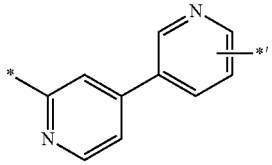

Formula 2A

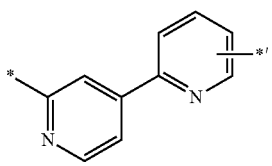

Formula 2B wherein
* may represent a point of connection to Ar¹ and
*' may represent a point of connection to Ar².

In other embodiments, Formula 2 may be represented by Formula 2C corresponding to symmetric bipyridine moiety (in which the nitrogen atoms are located symmetrically across the bipyridine ring system):

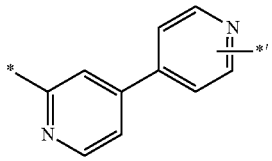

Formula 2C wherein
* may represent a point of connection to Ar¹ and
*' may represent a point of connection to Ar².

In some embodiments, the bipyridine moiety may be represented by Formula 2B-1 (corresponding to a 3,3'-substituted-2,4'-bipyridine moiety), Formula 2B-2 (corresponding to a 4,3'-substituted-2,4'-bipyridine moiety), Formula 2B-3 (corresponding to a 5,3'-substituted-2,4'-bipyridine moiety), and Formula 2B-4 (corresponding to a 6,3'-substituted-2,4'-bipyridine moiety):

Formula 2B-1

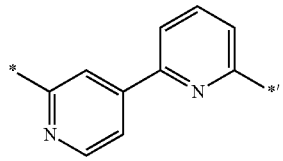

Formula 2B-2

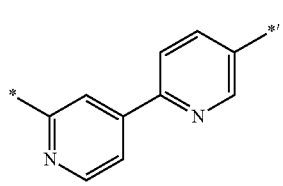

Formula 2B-3

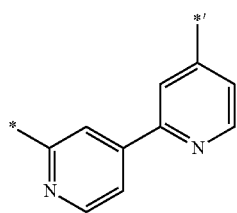

Formula 2B-4

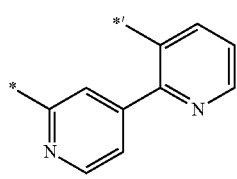

wherein

\* may represent a point of connection to Ar¹ and

\*' may represent a point of connection to Ar².

When the bipyridine moiety is represented by Formula 2B-1, group "-(L₁)$_{a1}$-B-(L₂)$_{a2}$-" in Formula 1 may be represented by the following structures:

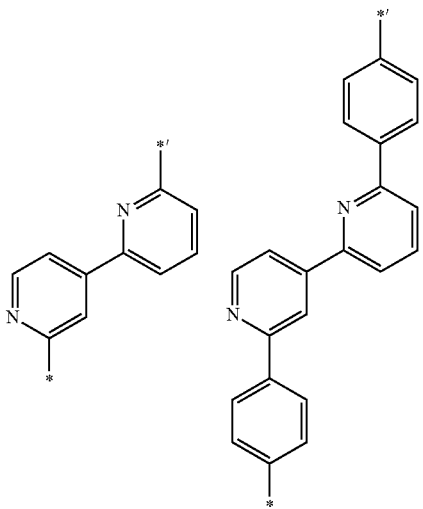

wherein

\* may represent a point of connection to Ar¹ and

\*' may represent a point of connection to Ar².

When the bipyridine moiety is represented by Formula 2B-2, group "-(L₁)$_{a1}$-B-(L₂)$_{a2}$-" in Formula 1 may be represented by the following structures:

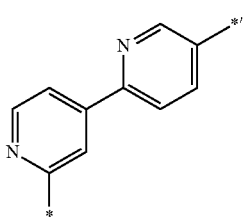

-continued

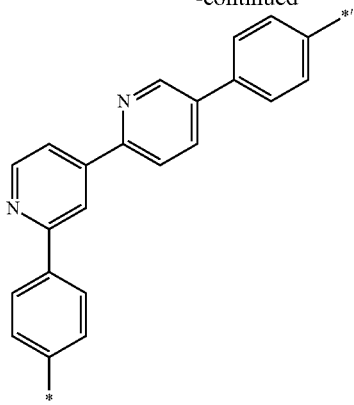

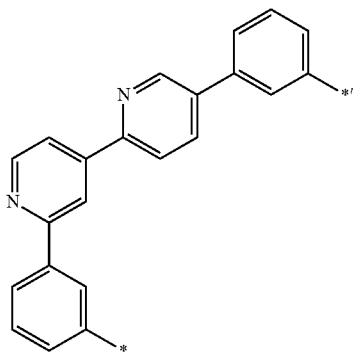

wherein

* may represent a point of connection to $Ar^1$ and

*' may represent a point of connection to $Ar^2$.

When the bipyridine moiety is represented by Formula 2B-3, group "-$(L_1)_{a1}$-B-$(L_2)_{a2}$-" in Formula 1 may be represented by the following structures:

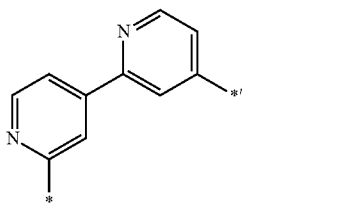

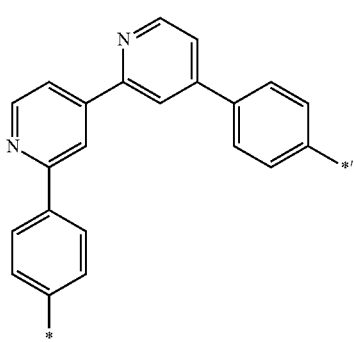

-continued

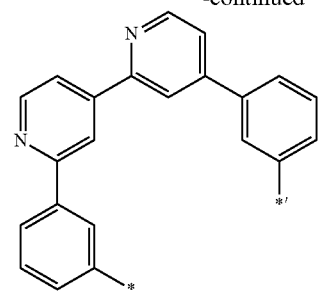

wherein

* may represent a point of connection to $Ar^1$ and

*' may represent a point of connection to $Ar^2$.

When the bipyridine moiety is represented by Formula 2B-4, group "-$(L_1)_{a1}$-B-$(L_2)_{a2}$-" in Formula 1 may be represented by the following structures:

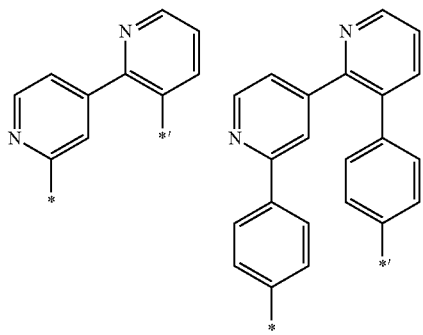

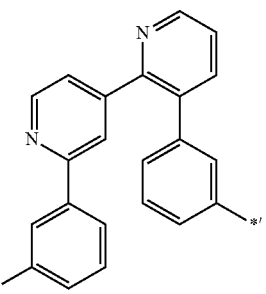

wherein

* may represent a point of connection to $Ar^1$ and

*' may represent a point of connection to $Ar^2$.

In some embodiments, the condensed cyclic compound may be represented by one of the following Compounds 1 to 26:
1
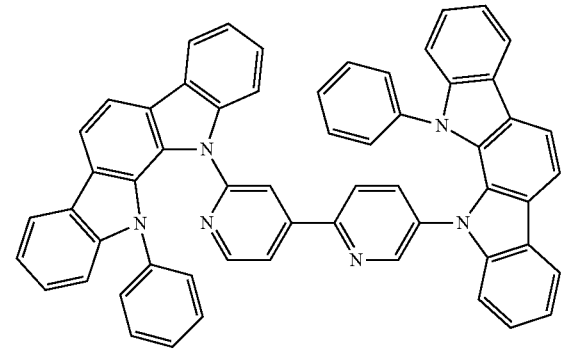
2
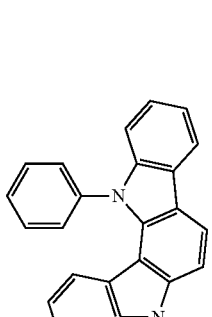
3
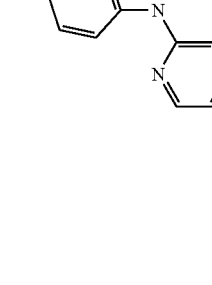
4
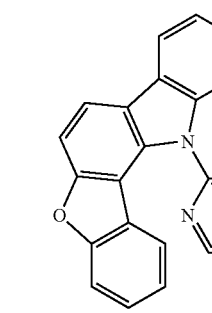
5
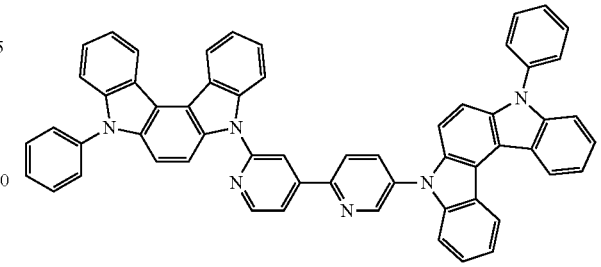
6
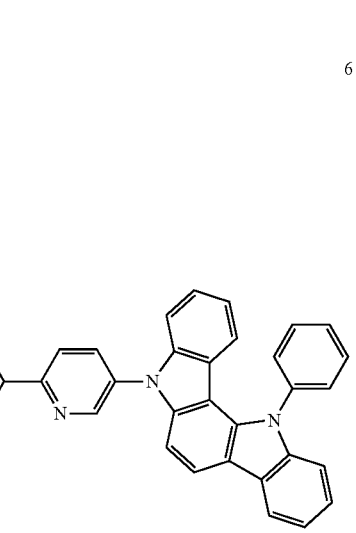
7
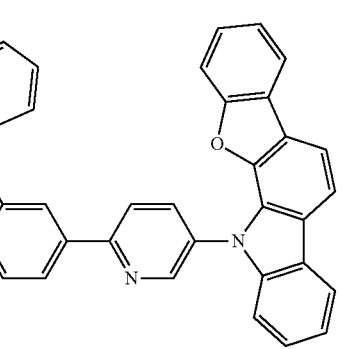
8
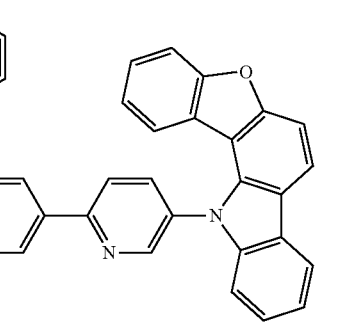

9
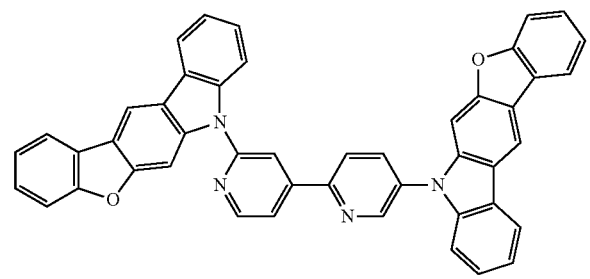
10
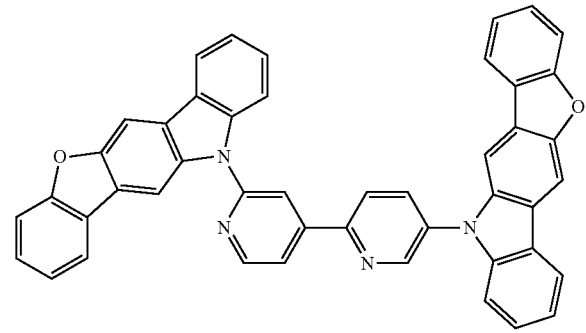
11
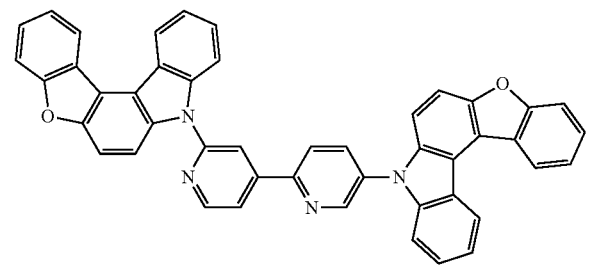
12
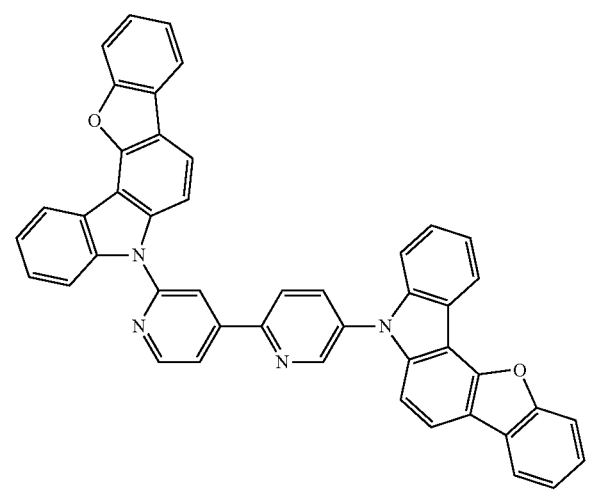
13
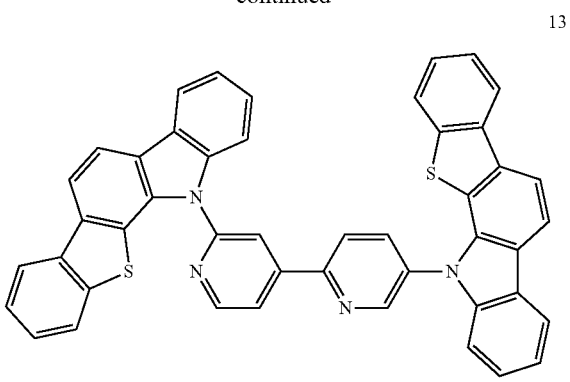
14
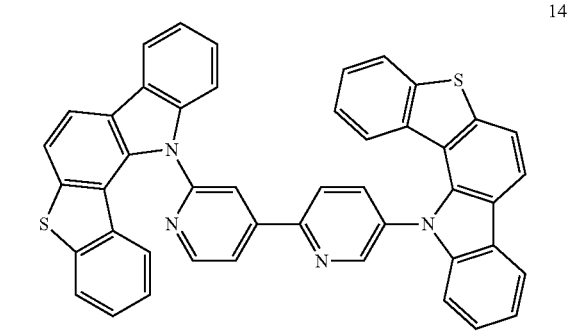
15
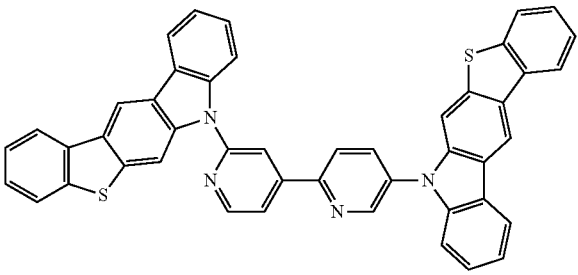
16
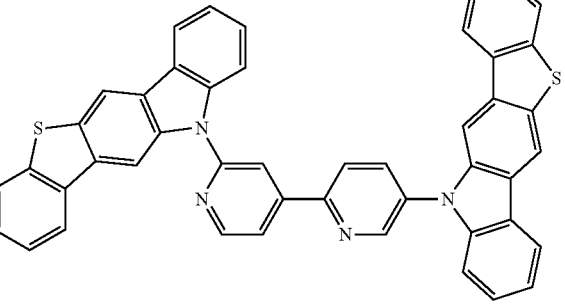
17
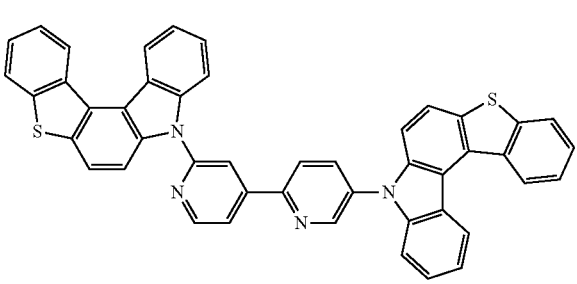

18
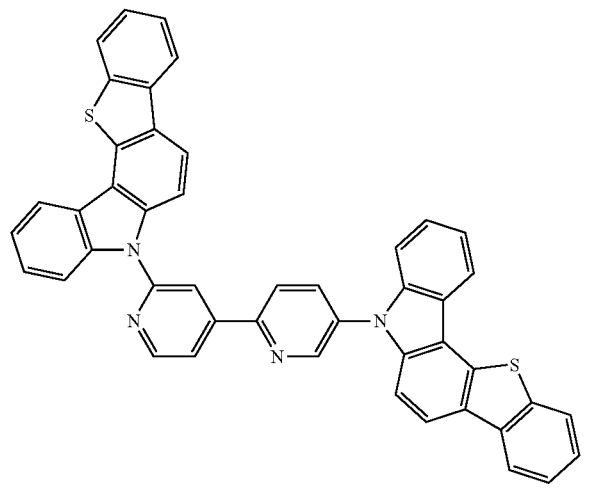
19
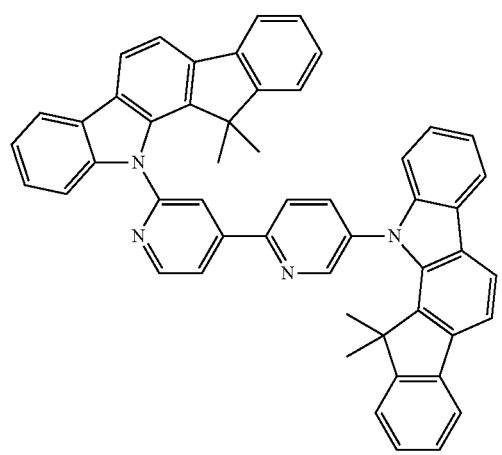
20
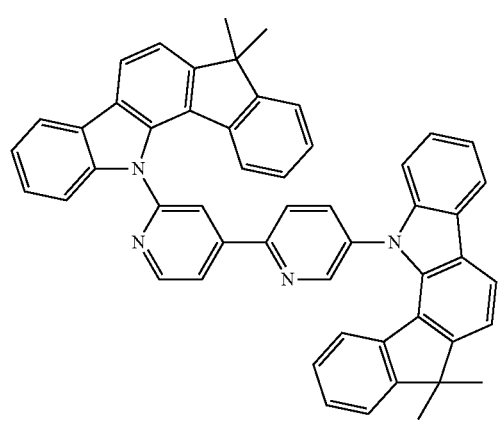
21
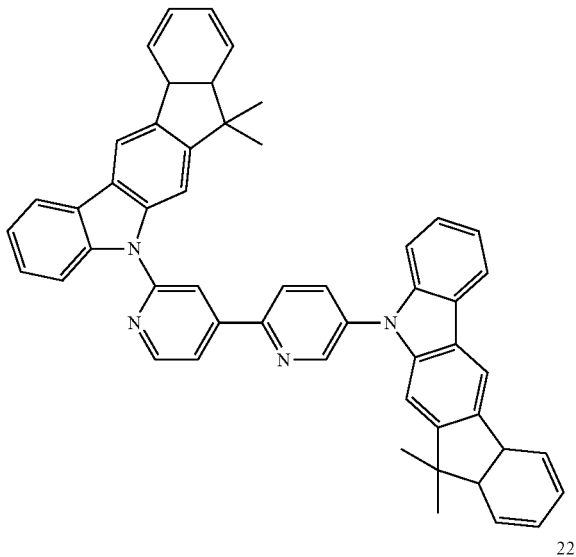
22
23
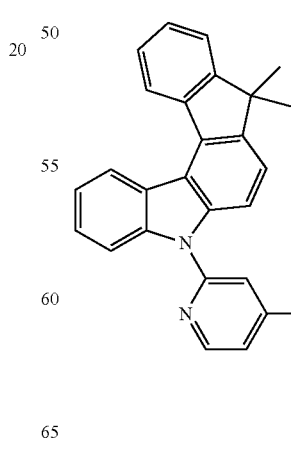

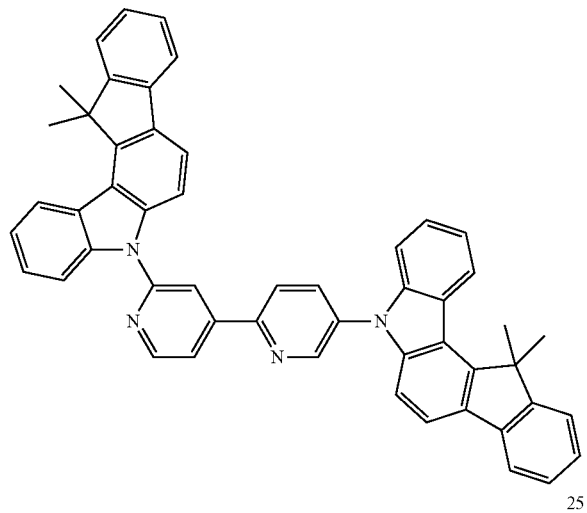

24

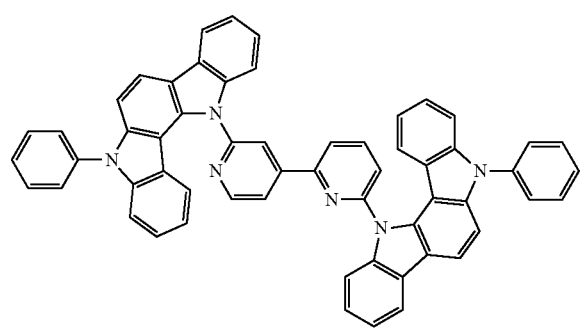

25

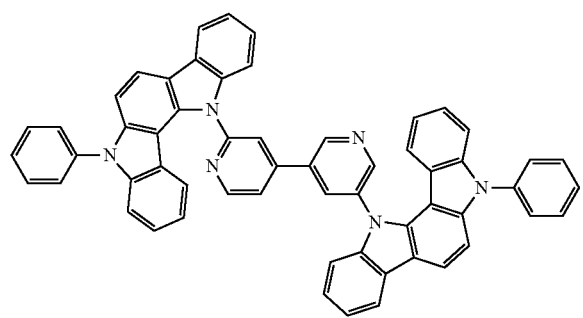

26

The condensed cyclic compounds according to the present embodiments includes a bipyridyl ring system, which may be symmetric or asymmetric. Accordingly, the condensed cyclic compound represented by Formula 1 may have a triplet ($T_1$) energy level that is suitable for an electronic device, for example, for use as a material for an organic light-emitting device (for example, a host material in an emission layer). Further, the advantage of using asymmetric bipyridine core is to make delta EST (which is a key parameter for TADF material) value smaller so that TADF characteristic can be enhanced or maximized, compared to symmetric bipyridine core-based analogues.

The condensed cyclic compound represented by Formula 1 may have a relatively small difference between $S_1$ (singlet) energy and $T_1$ (triplet) energy. Accordingly, the condensed cyclic compound represented by Formula 1 may be used as a thermally activated delayed fluorescence emitter (TADF emitter).

For example, the highest occupied molecular orbital (HOMO), lowest unoccupied molecular orbital (LUMO), $T_1$ and $S_1$ energy levels of Compounds 1-6, 8-12, and 15-26 were simulated by using Gaussian program DFT method (the structure is optimized at B3LYP, 6-31G(d,p) level), and simulation evaluation results are shown in Table 1 below:

TABLE 1

| Compound | HOMO | LUMO | S1 | T1 | ΔST | F |
|---|---|---|---|---|---|---|
| 1 | −5.11504 | −1.69204 | 2.8953 | 2.7599 | 0.1354 | 0.0069 |
| 2 | −5.07259 | −1.76470 | 2.8369 | 2.7696 | 0.0673 | 0.0066 |
| 3 | −5.03721 | −1.80769 | 2.7640 | 2.6314 | 0.1326 | 0.0298 |
| 4 | −4.89054 | −1.73504 | 2.6926 | 2.5395 | 0.1531 | 0.0482 |
| 5 | −4.86823 | −1.82239 | 2.6184 | 2.4876 | 0.1308 | 0.0432 |
| 6 | −4.97027 | −1.85749 | 2.6639 | 2.5331 | 0.1308 | 0.0425 |
| 8 | −5.49356 | −1.99001 | 2.9793 | 2.8180 | 0.1613 | 0.0262 |
| 9 | −5.25437 | −1.94130 | 2.8493 | 2.6615 | 0.1878 | 0.0590 |
| 10 | −5.29056 | 1.92416 | 2.8794 | 2.6747 | 0.2047 | 0.0469 |
| 11 | −5.27287 | −1.98348 | 2.8130 | 2.6381 | 0.1749 | 0.0538 |
| 12 | −5.24675 | −1.96879 | 2.8200 | 2.6459 | 0.1741 | 0.0576 |
| 15 | −5.2511 | −1.96607 | 2.8265 | 2.6486 | 0.1779 | 0.0569 |
| 16 | −5.27559 | −1.95409 | 2.8429 | 2.6699 | 0.1730 | 0.0432 |
| 17 | −5.23069 | −2.01995 | 2.7618 | 2.6162 | 0.1456 | 0.0403 |
| 18 | −5.29845 | −1.99328 | 2.8472 | 2.6702 | 0.1770 | 0.0562 |
| 19 | −5.28185 | −2.18023 | 2.6609 | 2.6343 | 0.0266 | 0.0082 |
| 20 | −5.32403 | −1.81994 | 2.9746 | 2.7678 | 0.2068 | 0.0180 |
| 21 | −5.26226 | −1.89314 | 2.8942 | 2.7298 | 0.1644 | 0.0223 |
| 22 | −5.29899 | −1.84851 | 2.9774 | 2.7214 | 0.2560 | 0.0425 |
| 23 | −5.13109 | −1.92906 | 2.7363 | 2.5898 | 0.1465 | 0.0389 |
| 24 | −5.0666 | −1.94511 | 2.6749 | 2.5337 | 0.1412 | 0.0491 |
| 25 | −4.9363 | −1.7699 | 2.6848 | 2.6359 | 0.0489 | 0.0017 |
| 26 | −5.1161 | −1.6420 | 2.9873 | 2.8966 | 0.0907 | 0.0025 |

A synthesis method for the condensed cyclic compound represented by Formula 1 may be understood by one of ordinary skill in the art by referring to Synthesis Examples.

Accordingly, the condensed cyclic compound represented by Formula 1 is suitable for an organic layer of an organic light-emitting device, for example, for use as a host or emitter (for example, a TADF emitter) of an emission layer in the organic layer. Thus, in another aspect, provided is an organic light-emitting device including:

a first electrode;

a second electrode; and an organic layer disposed between the first electrode and the second electrode, wherein the organic layer including an emission layer and at least one of the condensed cyclic compounds represented by Formula 1.

Due to the inclusion of the condensed cyclic compound represented by Formula 1, the organic light-emitting device may have a low driving voltage, high efficiency, high luminance, high quantum luminescent efficiency, and long lifespan.

The condensed cyclic compound represented by Formula 1 may be used between a pair of electrodes that constitute an organic light-emitting device. For example, the condensed cyclic compound may be included in at least one selected from an emission layer, a hole transport region (for example, including at least one selected from a hole injection layer, a hole transport layer, and an electron blocking layer) disposed between a first electrode and the emission layer, and an electron transport region (for example, including at least one selected from a hole blocking layer, an electron transport layer, and an electron injection layer) disposed between the emission layer and a second electrode.

For example, the condensed cyclic compound represented by Formula 1 may be included in the emission layer. The condensed cyclic compound included in the emission layer may act as a host, and the emission layer may further include a dopant (a fluorescent dopant or a phosphorescent dopant). The emission layer may be a blue emission layer emitting blue light or sky-blue light. In an embodiment, the condensed cyclic compound represented by Formula 1 may be included in the emission layer, the emission layer may further include a phosphorescent dopant, and the emission layer may emit blue light. In another embodiment, the condensed cyclic compound represented by Formula 1 may be included in the emission layer, the emission layer may further include a phosphorescent dopant, and the emission layer may emit sky-blue light.

In some embodiments, the condensed cyclic compound represented by Formula 1 may be included in the emission layer, and the condensed cyclic compound may be a TADF emitter. In some embodiments, the emission layer may include the condensed cyclic compound represented by Formula 1 alone. In some embodiments, the emission layer may further include, in addition to the condensed cyclic compound represented by Formula 1, a host and/or a dopant.

The term "organic layer" as used herein refers to a single layer and/or a plurality of layers between the first electrode and the second electrode of an organic light-emitting device. The "organic layer" may include, in addition to an organic compound, an organometallic complex including metal.

FIG. 1 is a schematic view of an organic light-emitting device 10 according to an embodiment. Hereinafter, the structure of an organic light-emitting device according to an embodiment and a method of manufacturing an organic light-emitting device according to an embodiment will be described in connection with FIG. 1. The organic light-emitting device 10 may include a first electrode 11, an organic layer 15, and a second electrode 19, which are sequentially stacked.

In FIG. 1, a substrate may be additionally disposed under the first electrode 11 or above the second electrode 19. For use as the substrate, any substrate that is used in general organic light-emitting devices may be used, and the substrate may be a glass substrate or transparent plastic substrate, each with excellent mechanical strength, thermal stability, transparency, surface smoothness, ease of handling, and water-resistance.

The first electrode 11 may be formed by depositing or sputtering a material for forming the first electrode on the substrate. The first electrode 11 may be an anode. The material for the first electrode 11 may be selected from materials with a high work function to allow holes be easily provided. The first electrode 11 may be a reflective electrode or a transparent electrode. The material for the first electrode may be, for example, indium tin oxide (ITO), indium zinc oxide (IZO), tin oxide ($SnO_2$), and zinc oxide (ZnO). In some embodiments, magnesium (Mg), aluminum (Al), aluminum-lithium (Al—Li), calcium (Ca), magnesium-indium (Mg—In), or magnesium-silver (Mg—Ag) may be used as the material for the first electrode.

The first electrode 11 may have a single-layer structure or a multi-layer structure including two or more layers. For example, the first electrode 11 may have a three-layered structure of ITO/Ag/ITO, but the structure of the first electrode 11 is not limited thereto.

An organic layer 15 may be disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In some embodiments, the hole transport region may have a structure of hole injection layer/hole transport layer or hole injection layer/hole transport layer/electron blocking layer, which are sequentially stacked in this stated order from the first electrode 11.

A hole injection layer hole injection layer may be formed on the first electrode 11 by using various methods, such as vacuum deposition, spin coating, casting, or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100 to about 500° C., a vacuum pressure of about 10' to about 10' torr, and a deposition rate of about 0.01 to about 100 Angstroms per second (Å/sec). However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylenedioxythiophene)/poly(4-styrene sulfonate) (PEDOT/PSS), polyaniline/camphor sulfonic acid (PANI/CSA), (polyaniline)/poly(4-styrene sulfonate)

(PANI/PSS), a compound represented by Formula 201 below, and a compound represented by Formula 202 below:
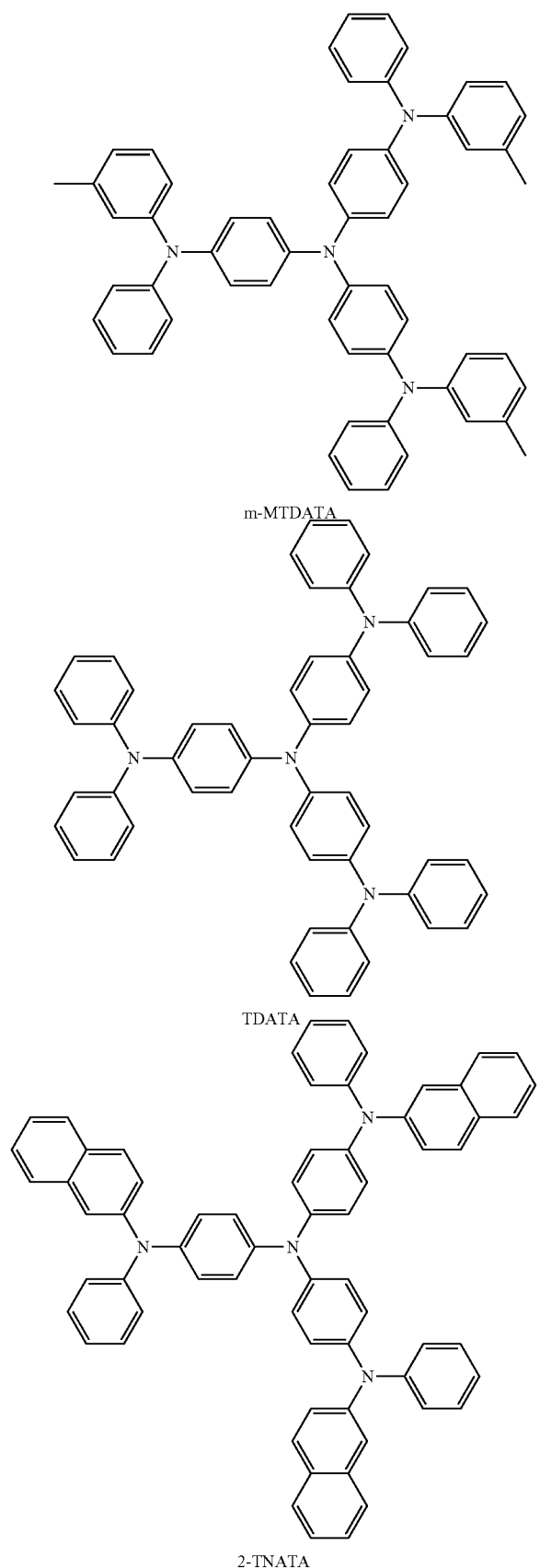
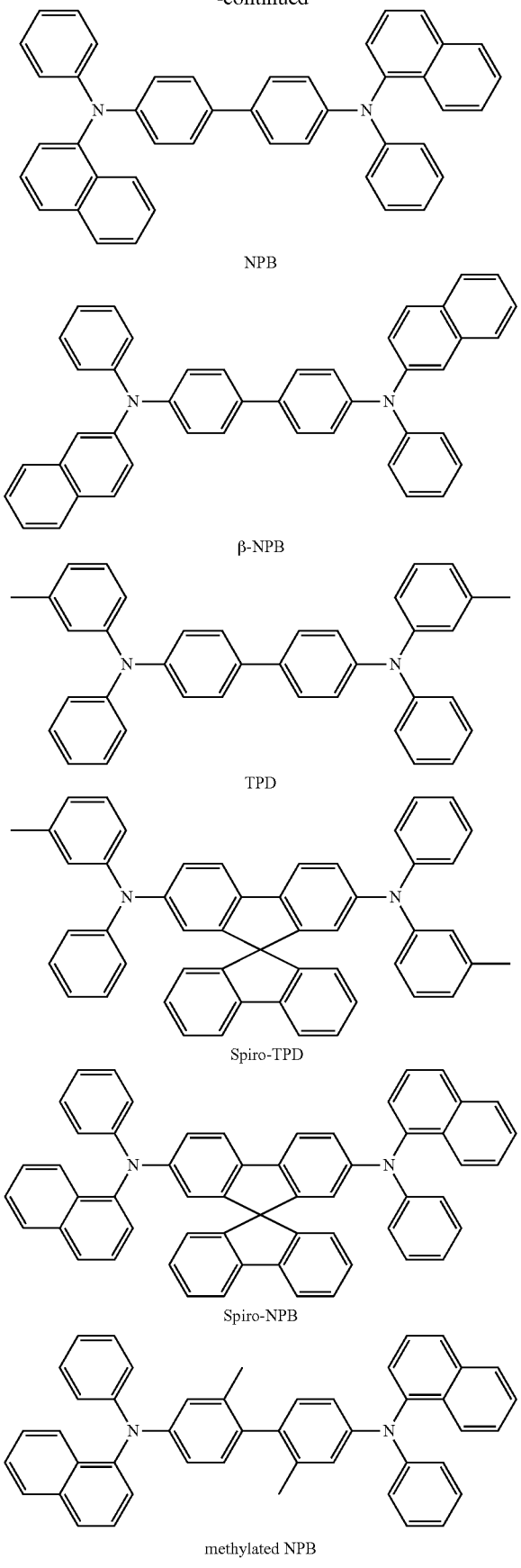

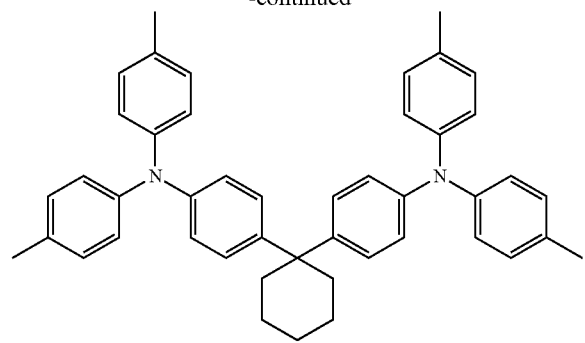

TAPC

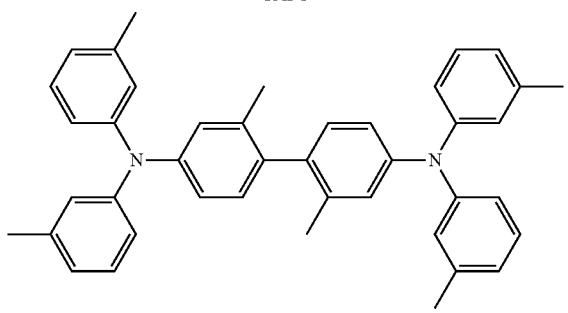

HMTPD

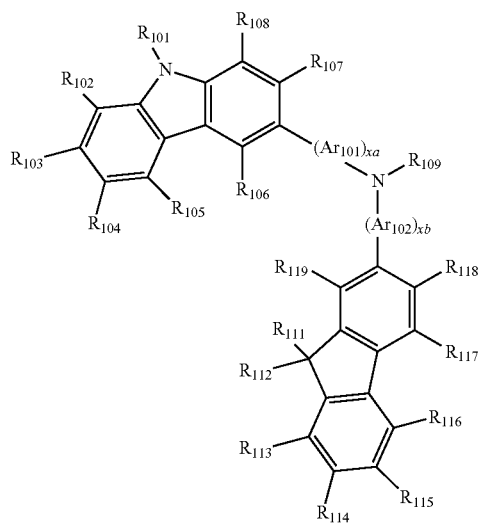

Formula 201

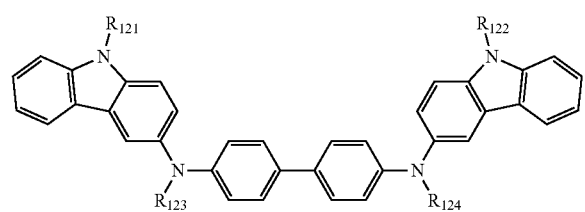

Formula 202

$Ar_{101}$ to $Ar_{102}$ in Formula 201 may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkyl group, a $C_3$-$C_{60}$ cycloalkenyl group, a $C_1$-$C_{10}$ heterocycloalkyl group, a $C_1$-$C_{60}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, and a $C_3$-$C_{60}$ heteroarylalkyl group.

In Formula 201, xa and xb may be each independently an integer of 0 to 5, or 0, 1, or 2. For example, xa is 1 and xb is 0, but xa and xb are not limited thereto.

$R_{101}$ to $R_{108}$, $R_{111}$ to $R_{119}$ and $R_{121}$ to $R_{124}$ in Formulae 201 and 202 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, and so on), or a $C_1$-$C_{10}$ alkoxy group (for example, a methoxy group, an ethoxy group, a propoxy group, a butoxy group, a pentoxy group, and so on);

a $C_1$-$C_{10}$ alkyl group or a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but they are not limited thereto.

$R_{109}$ in Formula 201 may be selected from a phenyl group, a naphthyl group, an anthracenyl group, and a pyridinyl group; and a phenyl group, a naphthyl group, an anthracenyl group, and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

According to an embodiment, the compound represented by Formula 201 may be represented by Formula 201A, but is not limited thereto:

Formula 201A

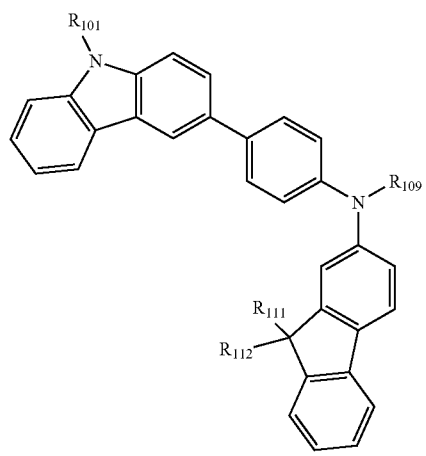

$R_{101}$, $R_{111}$, $R_{112}$, and $R_{109}$ in Formula 201A may be understood by referring to the description provided herein.

For example, the compound represented by Formula 201, and the compound represented by Formula 202 may include Compounds HT1 to HT20 illustrated below, but are not limited thereto.

HT1

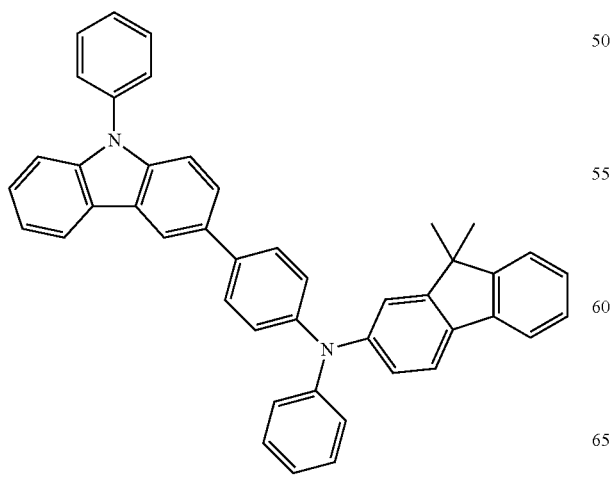

HT2

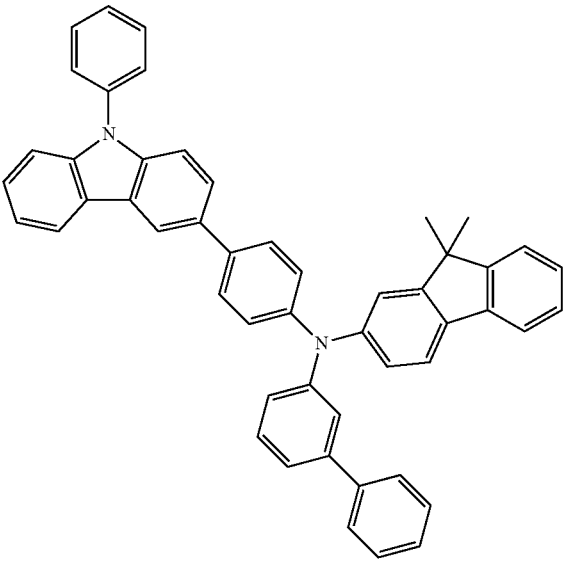

HT3

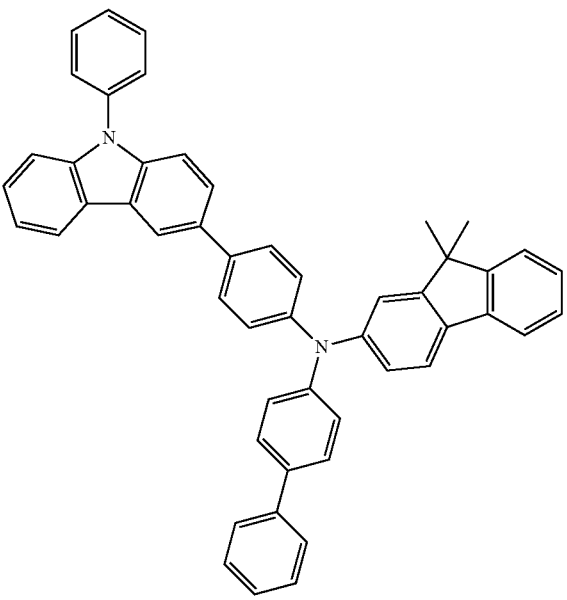

HT4
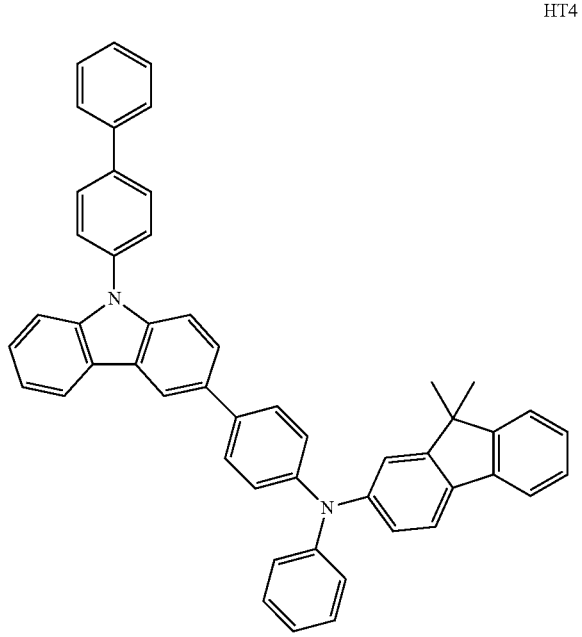
HT6
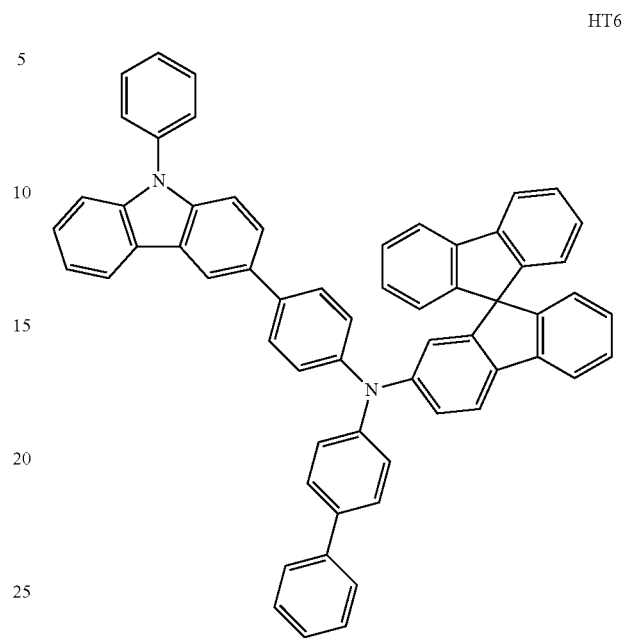
HT5
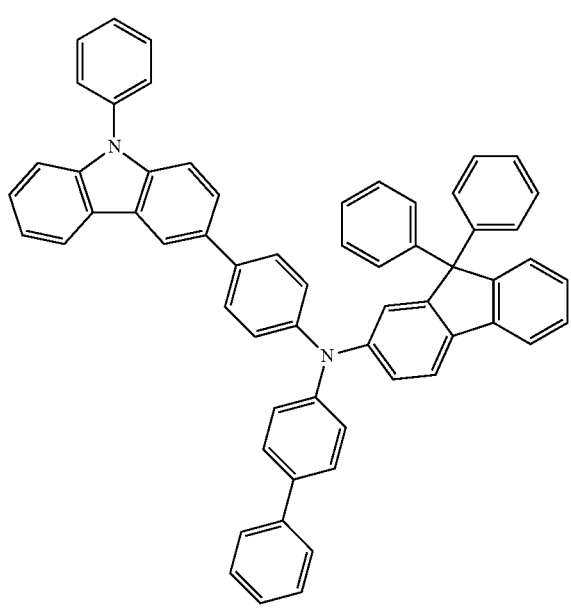
HT7
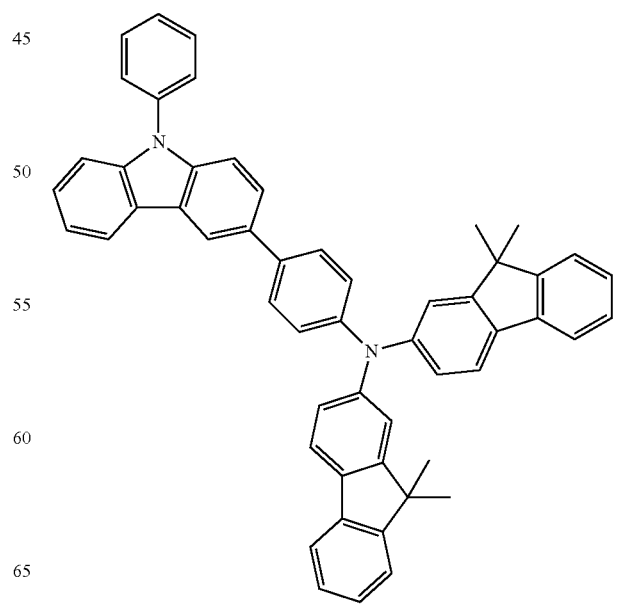

HT8
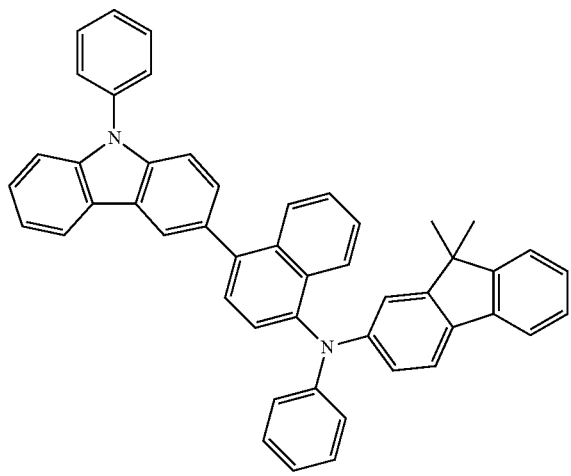
HT9
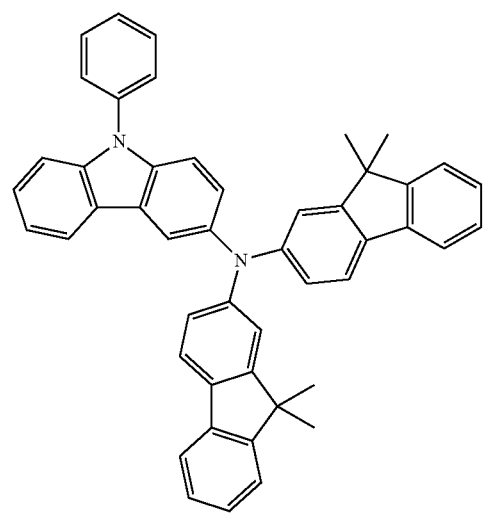
HT10
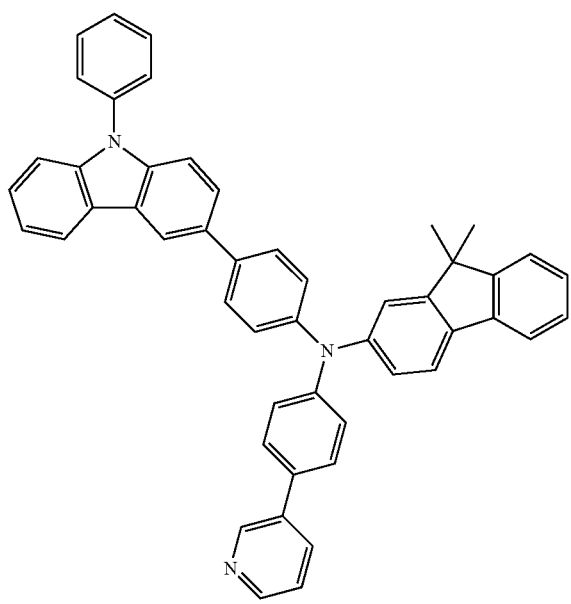
HT11
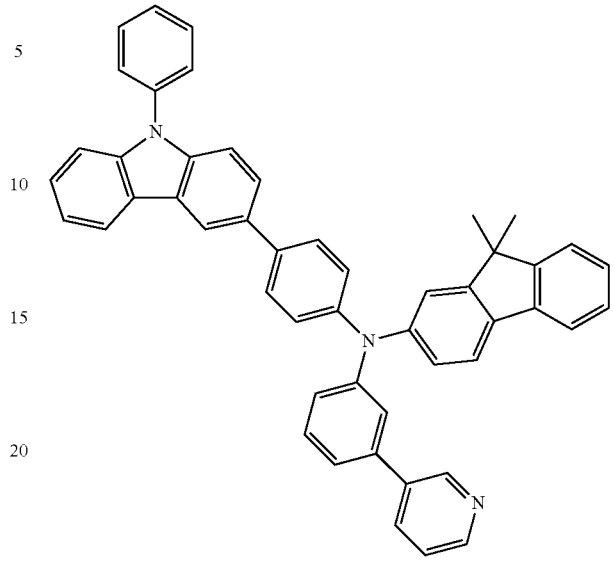
HT12
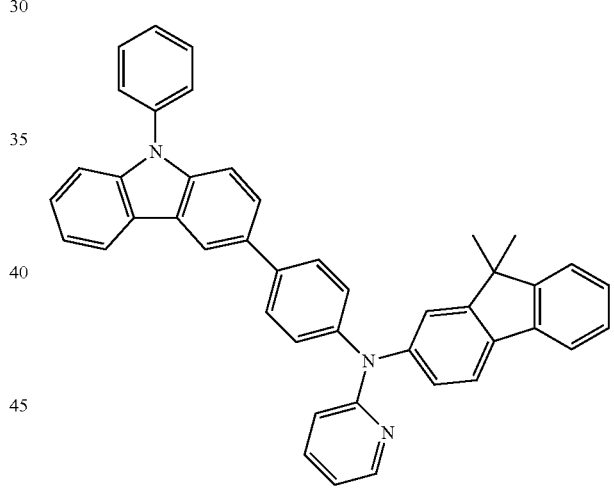
HT13
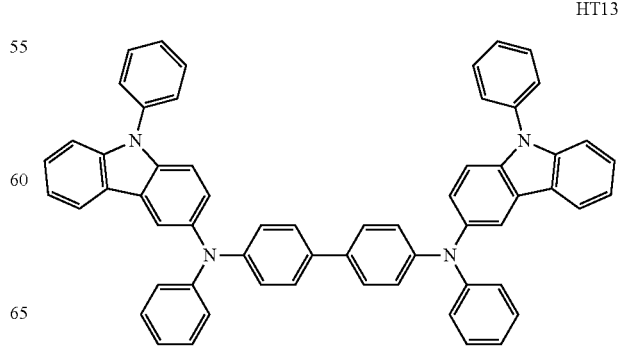

HT14
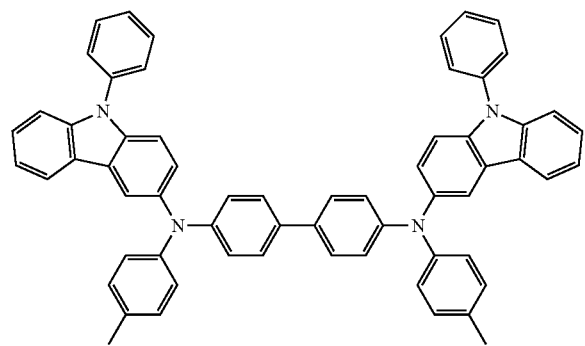

HT15
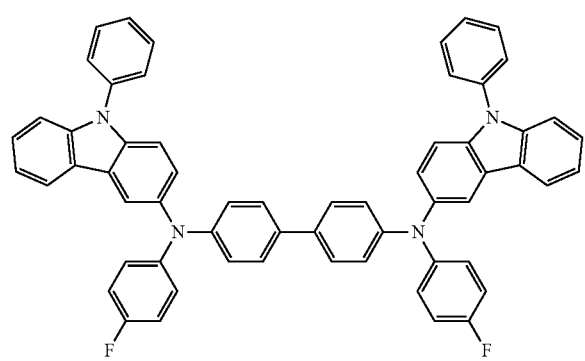

HT16
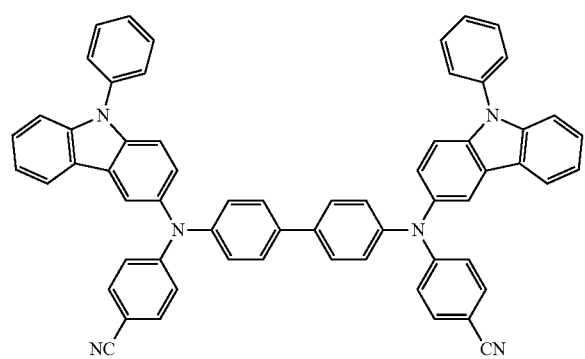

HT17
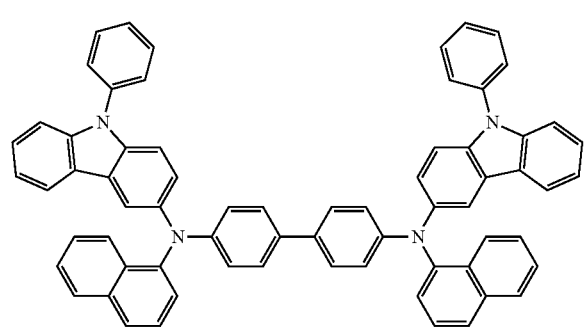

HT18
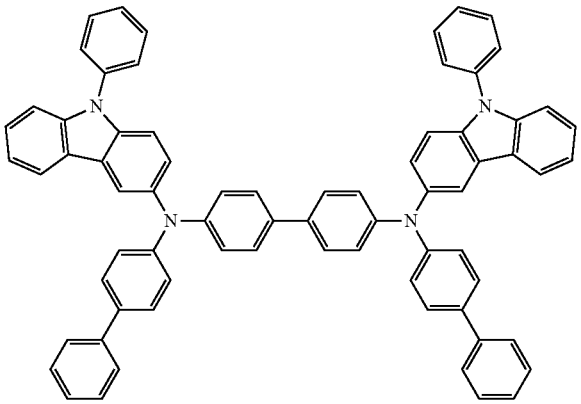

HT19
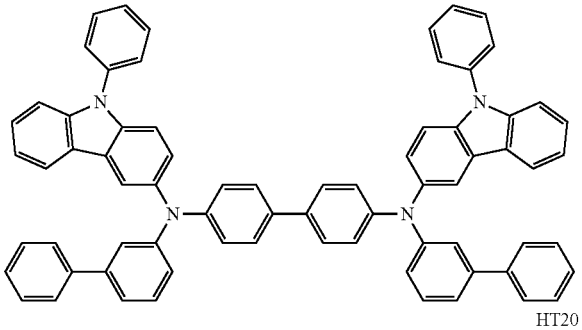

HT20

A thickness of the hole transport region may be in a range of about 100 Angstroms (Å) to about 10,000 Å, for example, about 100 Å to about 1,000 Å. When the hole transport region includes a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1,500 Å. While not wishing to be bound by a theory, it is understood that when the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1 or HP-1, but are not limited thereto:

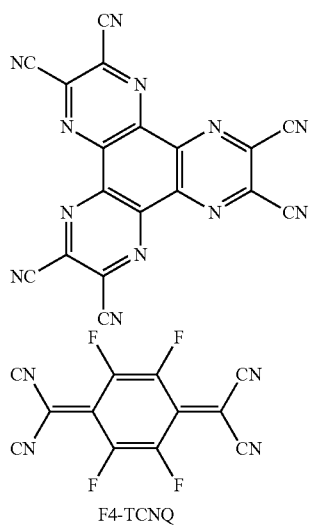

Compound HT-D1

F4-TCNQ

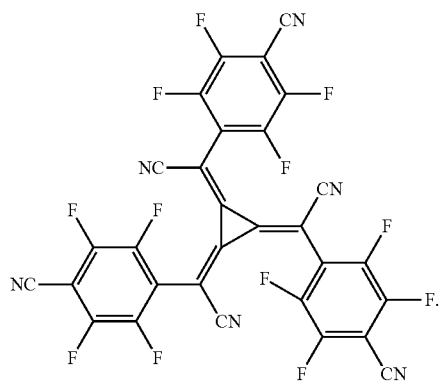

HP-1

The hole transport region may include a buffer layer.

Also, the buffer layer may compensate for an optical resonance distance according to a wavelength of light emitted from the emission layer, and thus, efficiency of a formed organic light-emitting device may be improved.

Then, an emission layer (EML) may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

The electron transport region may further include an electron blocking layer. The electron blocking layer may include, for example, mCP, but a material therefor is not limited thereto.

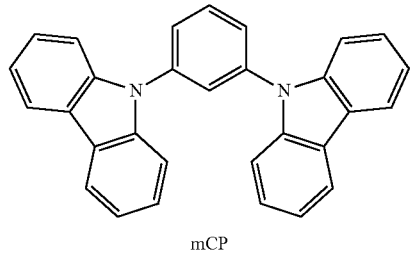 [SMILES: c1cc(-n2c3ccccc3c3ccccc32)cc(-n2c3ccccc3c3ccccc32)c1]

mCP

When the organic light-emitting device is a full color organic light-emitting device, the emission layer may be patterned into a red emission layer, a green emission layer, and a blue emission layer. In some embodiments, due to a stack structure including a red emission layer, a green emission layer, and/or a blue emission layer, the emission layer may emit white light.

The emission layer may include the condensed cyclic compound represented by Formula 1. The emission layer may include a dopant. The dopant may be at least one selected from a phosphorescent dopant and a fluorescent dopant.

In some embodiments, the emission layer may include the condensed cyclic compound represented by Formula 1 alone, and the condensed cyclic compound may be a TADF emitter.

In some embodiments, the emission layer may include the condensed cyclic compound represented by Formula 1, the condensed cyclic compound may be a TADF emitter, and the emission layer may further include a host.

For example, a host in the emission layer may include the condensed cyclic compound represented by Formula 1.

A dopant in the emission layer may be a fluorescent dopant that emits light according to a fluorescent emission mechanism or a phosphorescent dopant that emits light according to a phosphorescent emission mechanism.

According to an embodiment, the dopant in the emission layer may be a phosphorescent dopant, and the phosphorescent dopant may include an organometallic compound represented by Formula 81 below:

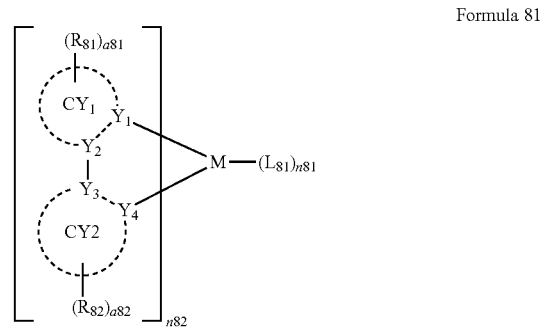

Formula 81 wherein in Formula 81,

M may be selected from iridium (Ir), platinum (Pt), osmium (Os), titanium (Ti), zirconium (Zr), hafnium (Hf), europium (Eu), terbium (Tb), and thulium (Tm);

$Y_1$ to $Y_4$ are each independently carbon (C) or nitrogen (N); $Y_1$ and $Y_2$ are linked via a single bond or a double bond, and $Y_3$ and $Y_4$ are linked via a single bond or a double bond;

$CY_1$ and $CY_2$ are each independently selected from a benzene, a naphthalene, a fluorene, a spiro-fluorene, an indene, a pyrrole, a thiophene, a furan, an imidazole, a pyrazole, a thiazole, an isothiazole, an oxazole, an isoxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzoxazole, an isobenzoxazole, a triazole, a tetrazole, an oxadiazole, a triazine, a dibenzofuran, and a dibenzothiophene, and $CY_1$ and $CY_2$ are optionally linked to each other through a single bond or an organic linking group;

$R_{81}$ and $R_{82}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_6P$ aryl group, a substituted or unsubstituted $C_6$-$C_{60}$ aryloxy group, a substituted or unsubstituted $C_6$-$C_6P$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, —$N(Q_1)(Q_2)$, —$Si(Q_3)(Q_4)(Q_5)$, and —$B(Q_6)(Q_7)$;

a81 and a82 are each independently an integer of 1 to 5;
n81 is an integer of 0 to 4;
n82 is 1, 2, or 3; and
$L_{81}$ is a monovalent organic ligand, a divalent organic ligand, or a trivalent organic ligand.

$R_{81}$ and $R_{82}$ may be understood by referring to the description provided herein in connection with $R_{11}$.

The phosphorescent dopant may include at least one selected from Compounds PD1 to PD78 and $FIr_6$, but embodiments are not limited thereto:

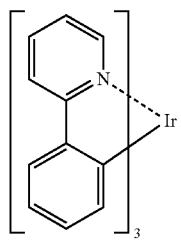

PD1

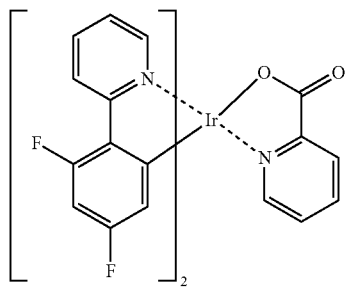

PD2

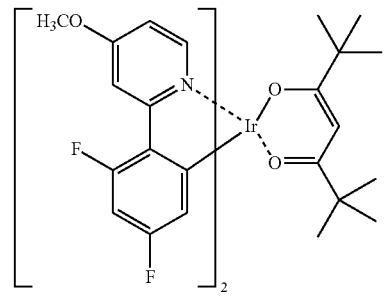

PD3

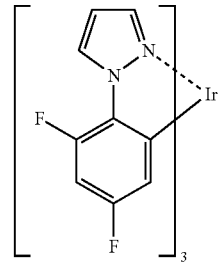

PD4

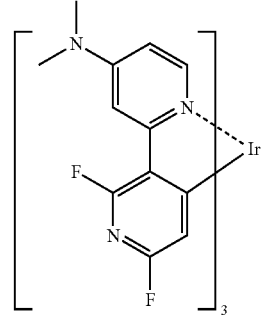

PD5

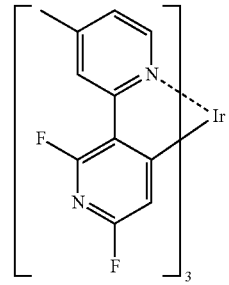

PD6

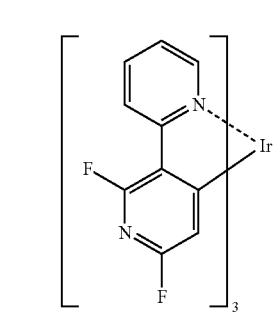

PD7

PD8
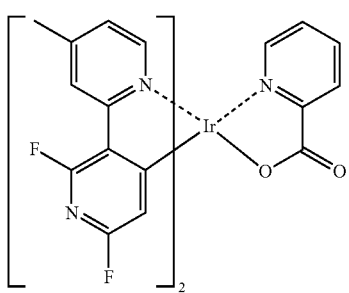
PD9
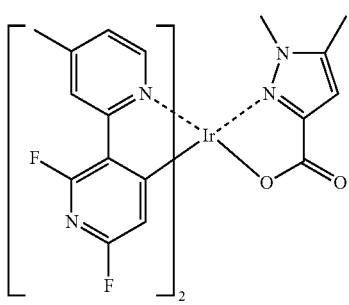
PD10
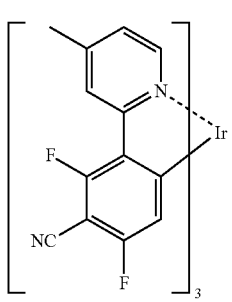
PD11
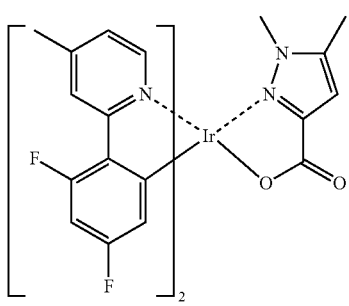
PD12
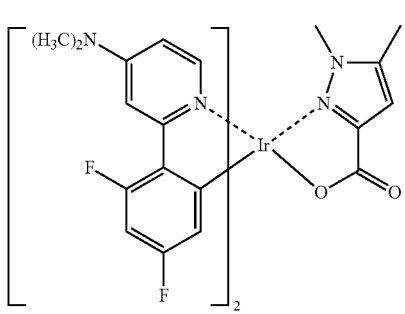
PD13
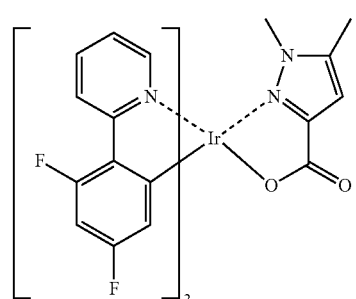
PD14
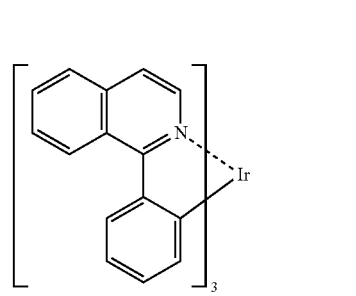
PD15
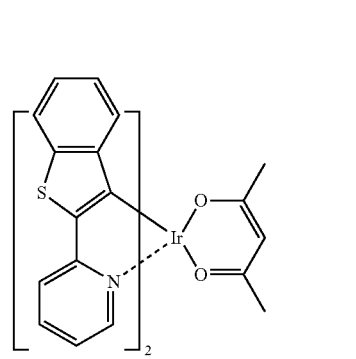
PD16
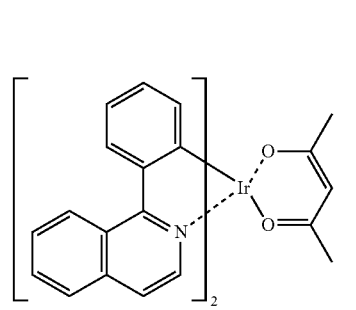
PD17
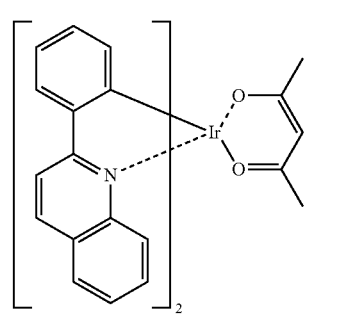

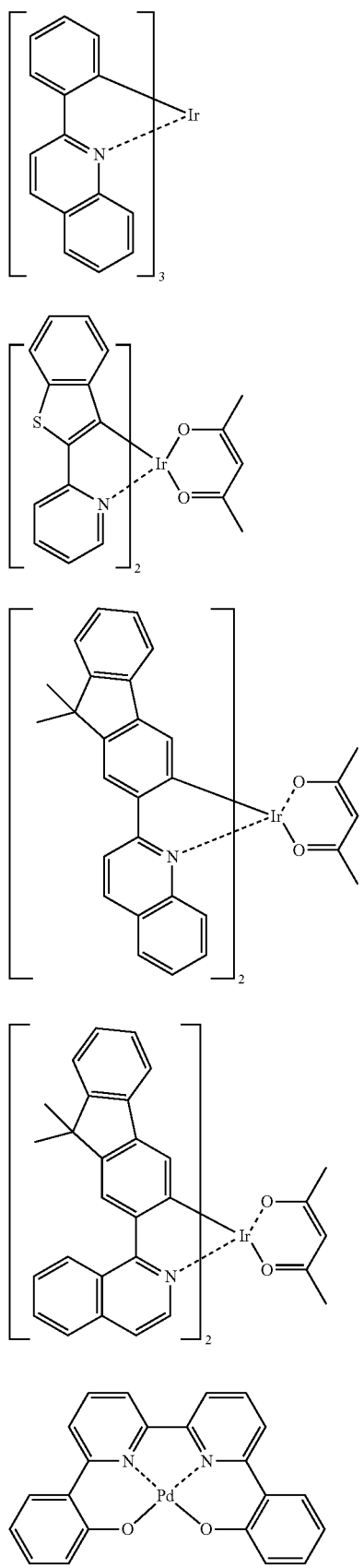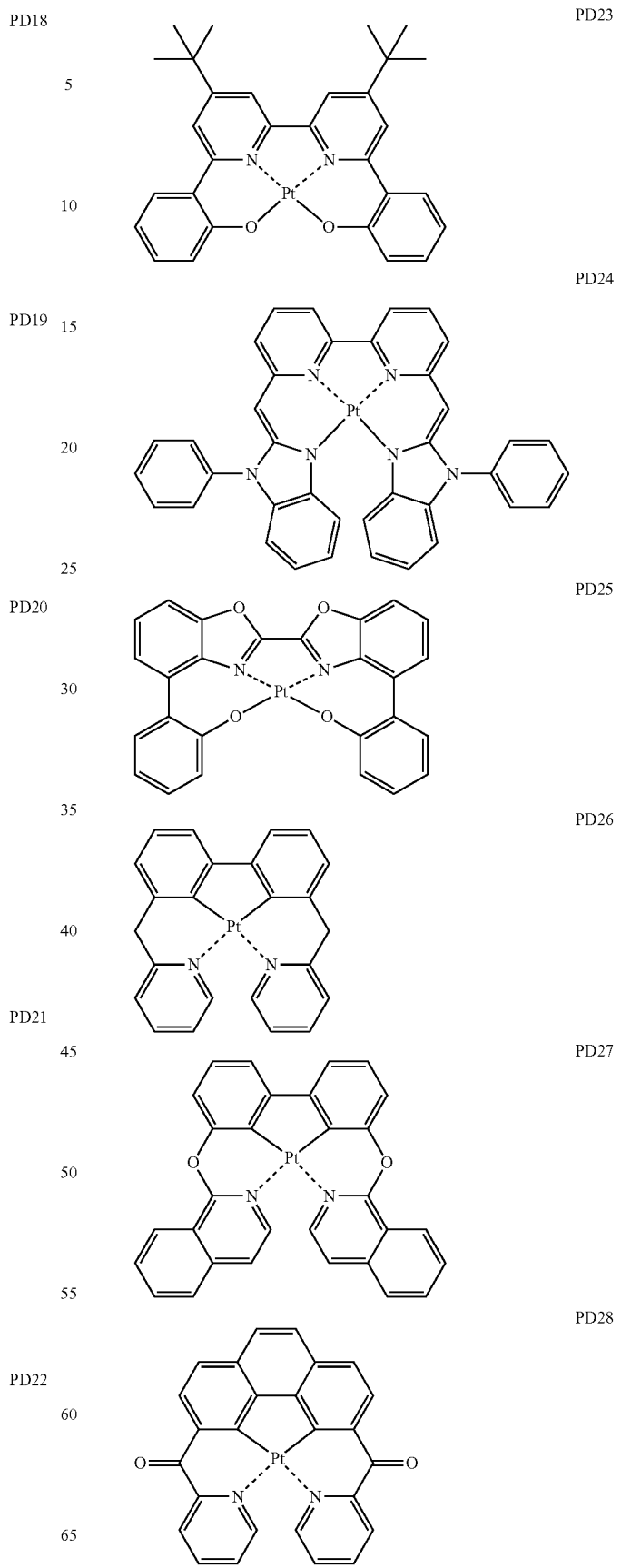

-continued
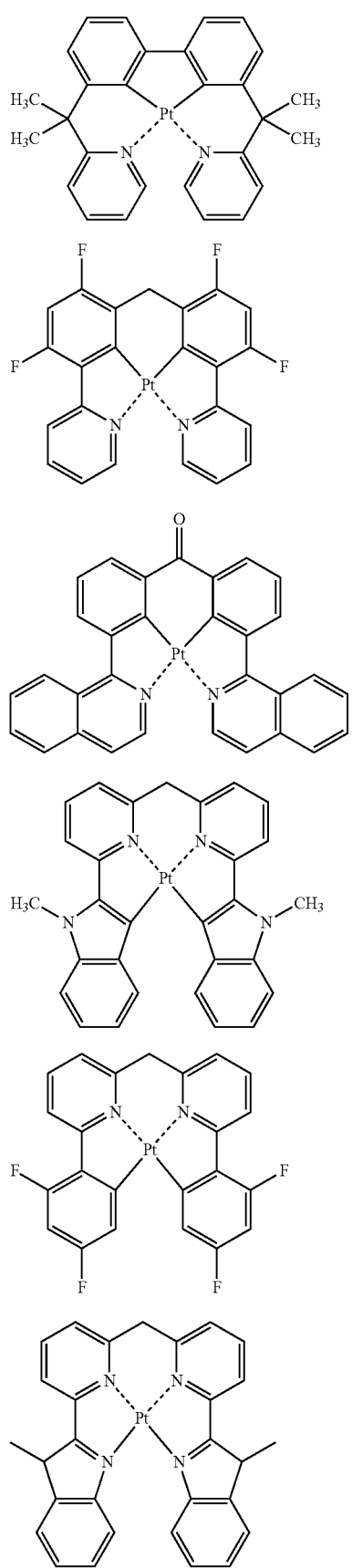
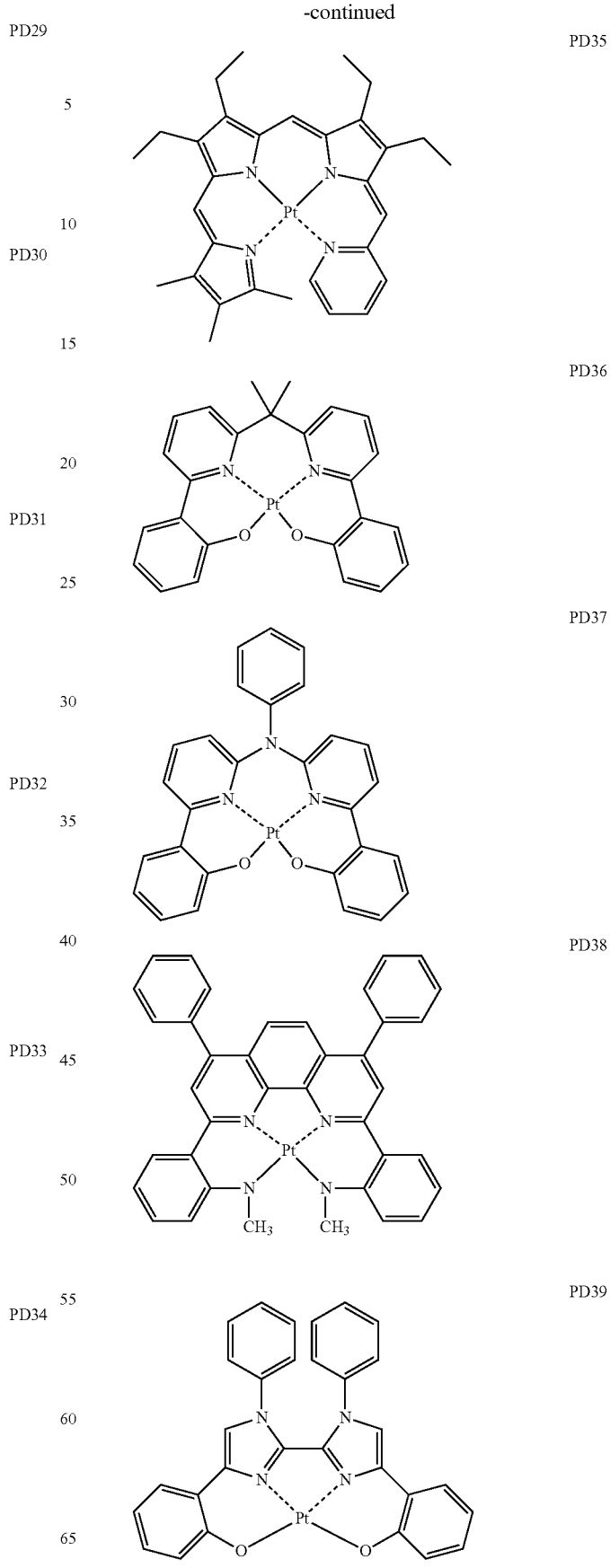

PD40
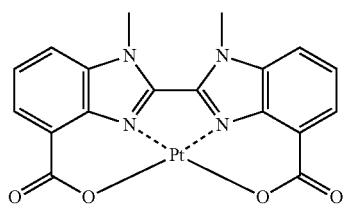
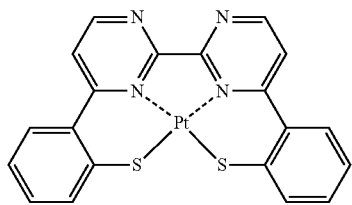
PD41
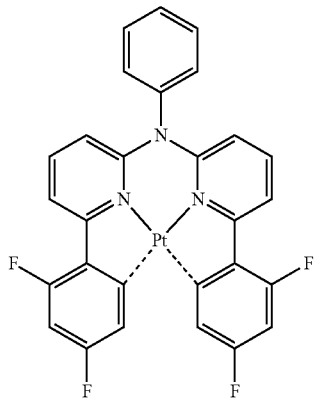
PD42
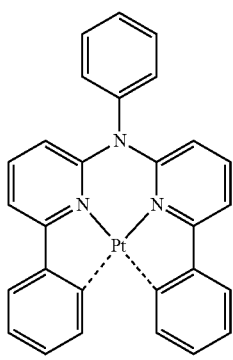
PD43
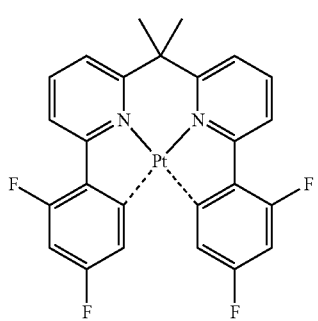
PD44
PD45
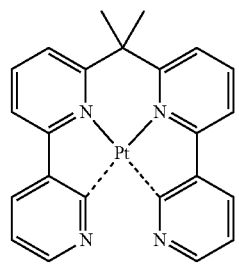
PD46
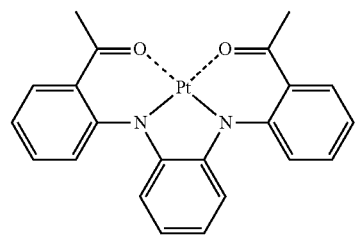
PD47
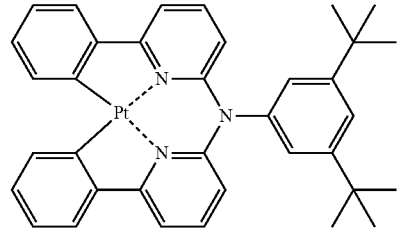
PD48
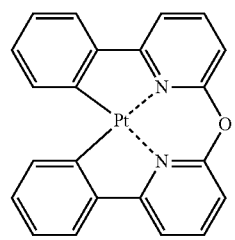
PD49
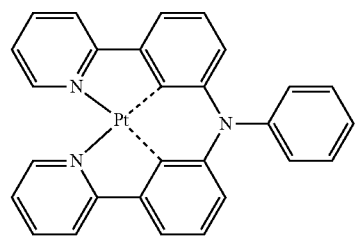
PD50
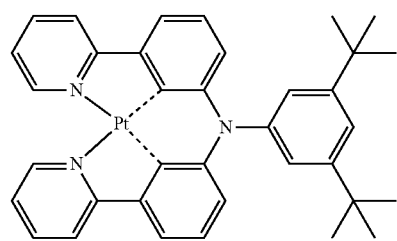

PD51 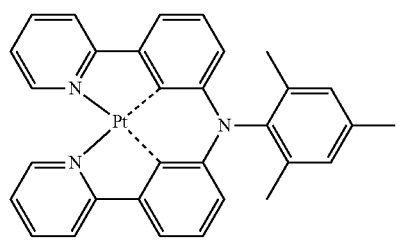
PD57 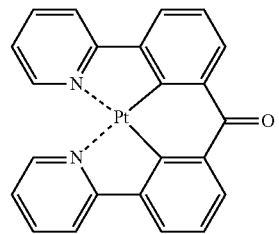
PD52 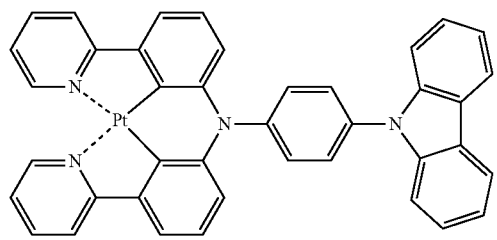
PD58 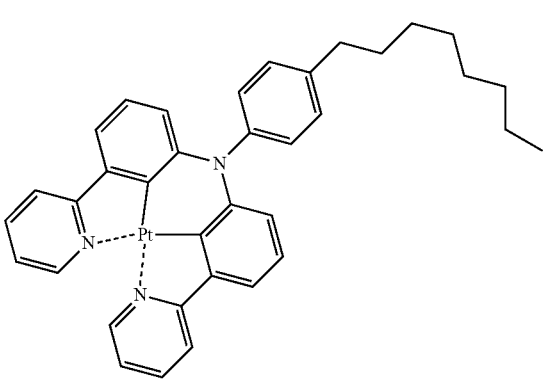
PD53 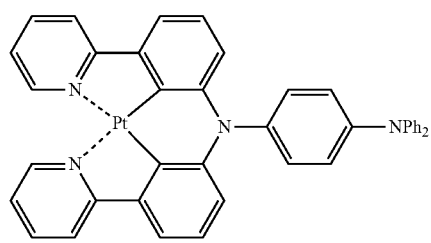
PD54 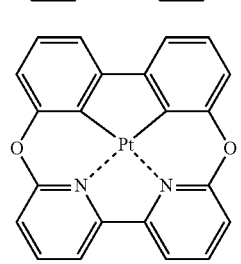
PD59 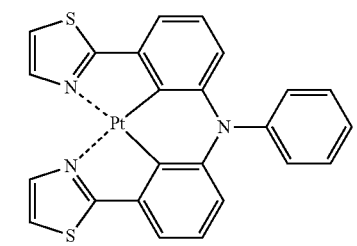
PD55 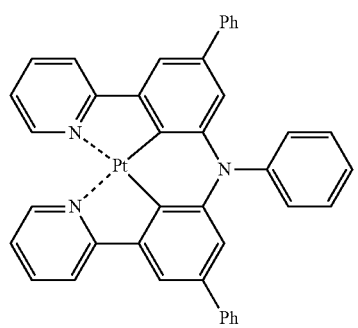
PD60 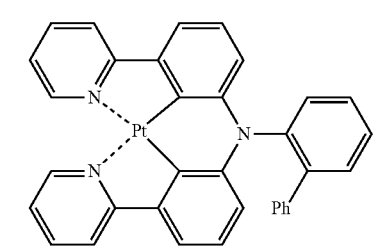
PD56 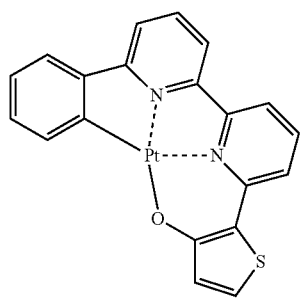
PD61 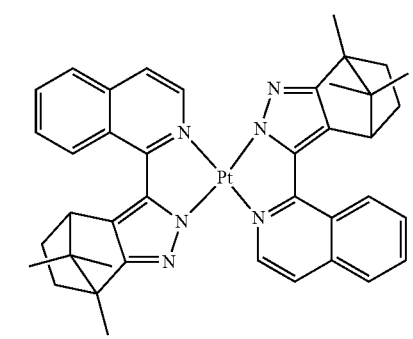

PD62 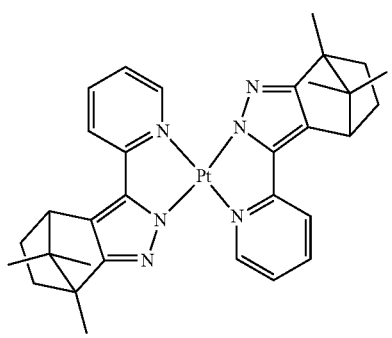
PD63 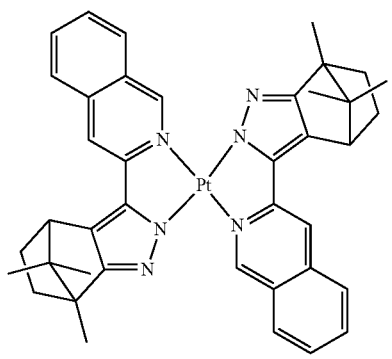
PD64 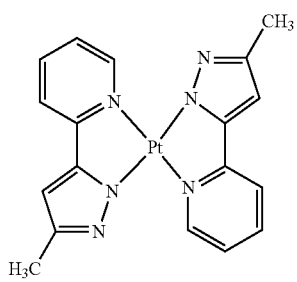
PD65 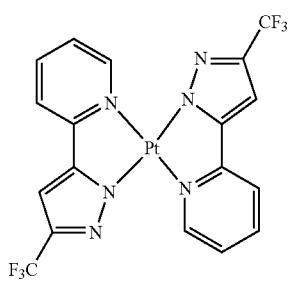
PD66 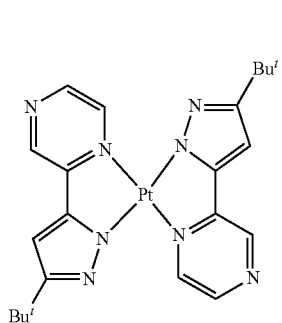
PD67 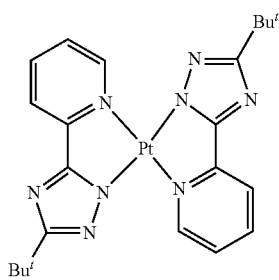
PD68 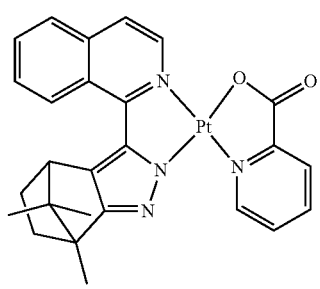
PD69 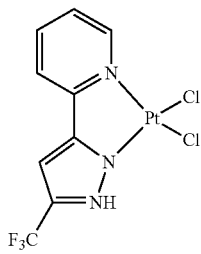
PD70 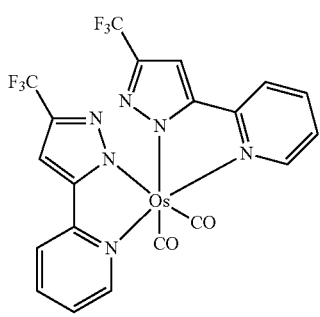
PD71 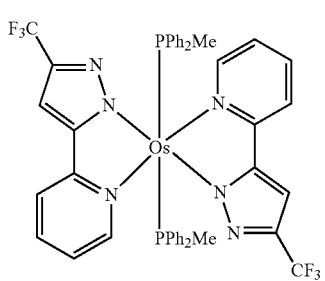

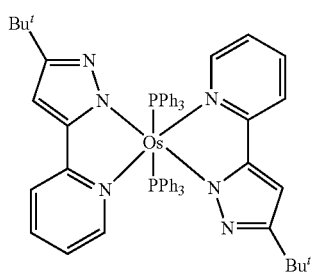
PD72

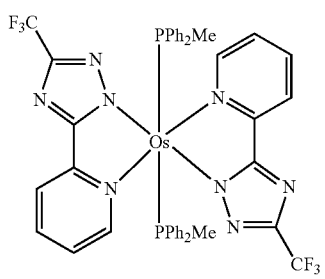
PD73

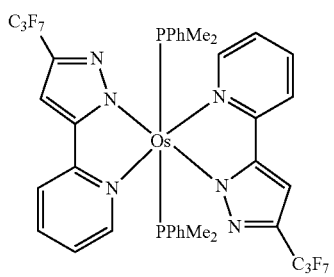
PD74

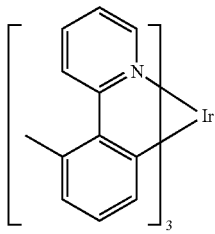
PD75

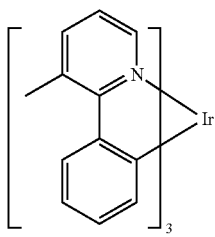
PD76

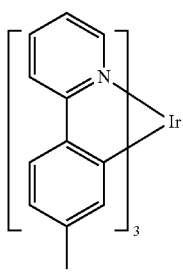
PD77

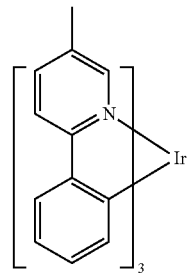
PD78

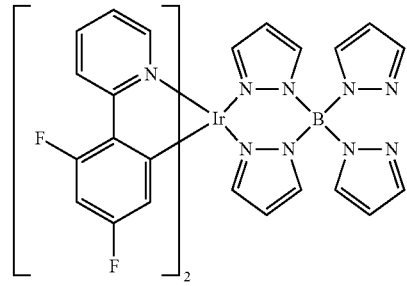
FIr6

In some embodiments, the phosphorescent dopant may include PtOEP:

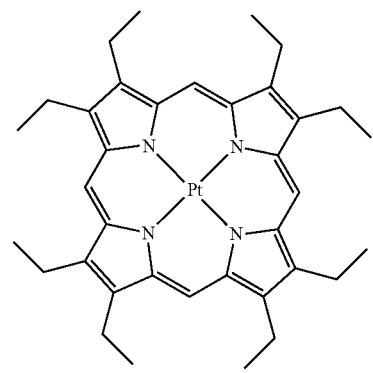
PtOEP

When the emission layer includes a host and a dopant, an amount of the dopant may be in a range of about 0.01 to about 20 parts by weight based on 100 parts by weight of the host, but is not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layer structure including two or more different materials.

Conditions for forming the hole blocking layer, the electron transport layer, and the electron injection layer which constitute the electron transport region may be understood by referring to the conditions for forming the hole injection layer.

When the electron transport layer includes a hole blocking layer, the hole blocking layer may include, for example, at least one selected from BCP and Bphen, but embodiments are not limited thereto.

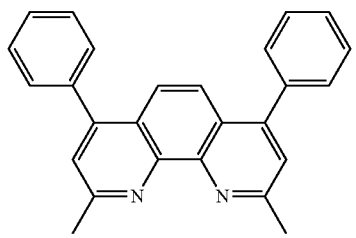

BCP

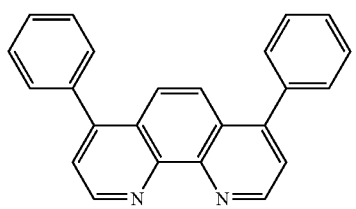

Bphen

A thickness of the hole blocking layer may be in a range of about 20 Å to about 1,000 Å, for example, about 30 Å to about 300 Å. When the thickness of the hole blocking layer is within these ranges, the hole blocking layer may have improved hole blocking ability without a substantial increase in driving voltage.

The electron transport layer may further include at least one selected from BCP, Bphen, Alq$_3$, Balq, TAZ, and NTAZ.

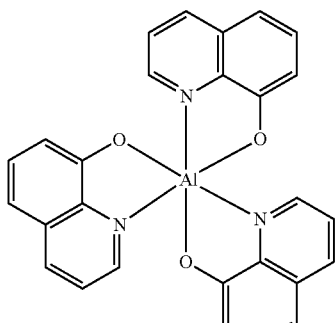

Alq$_3$

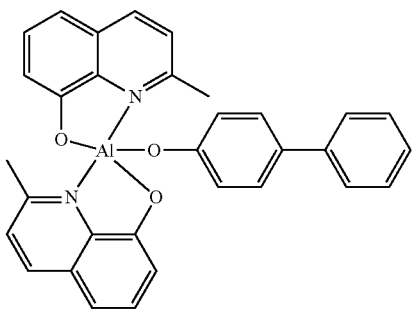

BAlq

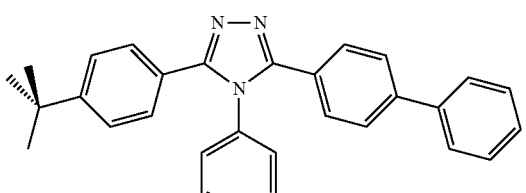

TAZ

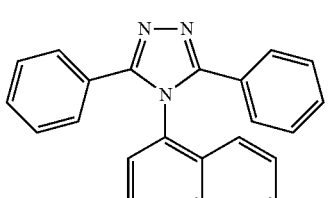

NTAZ

In some embodiments, the electron transport layer may include at least one selected from Compounds ET1, ET2, and ET3, but embodiments are not limited thereto:

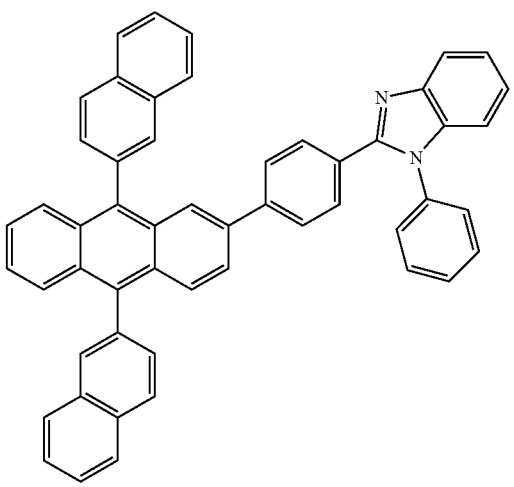

ET1

ET2

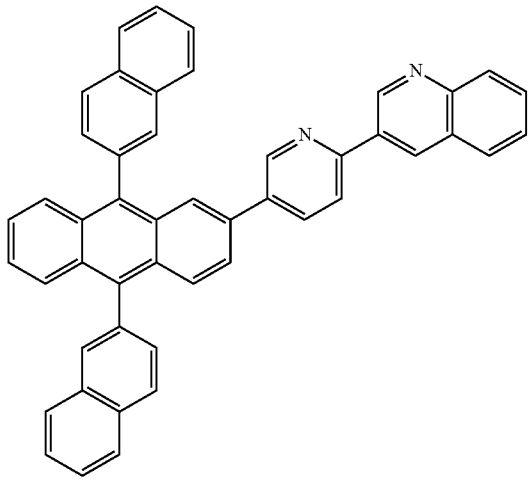

ET-D2

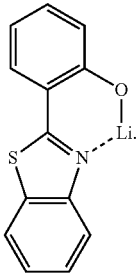

The electron transport layer may include an electron injection layer (EIL) that promotes flow of electrons from the second electrode 19 thereinto.

The electron injection layer may include at least one selected from, LiF, NaCl, CsF, $Li_2O$, BaO, and LiQ.

A thickness of the electron injection layer may be in a range of about 1 Å to about 100 Å, about 3 Å to about 90 Å. When the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be selected from metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as a material for forming the second electrode 19. In some embodiments, to manufacture a top emission type light-emitting device, a transmissive electrode formed using ITO or IZO may be used as the second electrode 19.

Hereinbefore, the organic light-emitting device has been described with reference to FIG. 1, but is not limited thereto.

A $C_1$-$C_{60}$ alkyl group as used herein refers to a linear or branched aliphatic hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —$OA_{101}$ (wherein $A_{101}$ is the $C_1$-$C_{60}$ alkyl group). Detailed examples thereof are a methoxy group, an ethoxy group, and an isopropyloxy group.

A $C_2$-$C_{60}$ alkenyl group as used herein refers to a hydrocarbon group formed by substituting at least one carbon double bond in the middle or at the terminal of the $C_2$-$C_{60}$ alkyl group. Detailed examples thereof are an ethenyl group, a propenyl group, and a butenyl group. A $C_2$-$C_{60}$ alkenylene group as used herein refers to a divalent group having the same structure as the $C_2$-$C_{60}$ alkenyl group.

ET3

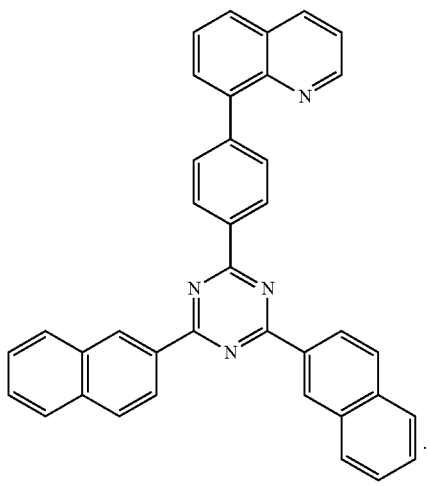

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a $L_1$ complex. The $L_1$ complex may include, for example, Compound ET-D1 (lithium quinolate, LiQ) or ET-D2:

ET-D1

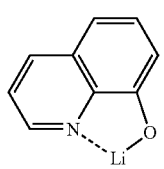

A $C_2$-$C_{60}$ alkynyl group as used herein refers to a hydrocarbon group formed by substituting at least one carbon trip bond in the middle or at the terminal of the $C_2$-$C_{60}$ alkyl group. Detailed examples thereof are an ethynyl group, and a propynyl group. A $C_2$-$C_{60}$ alkynylene group as used herein refers to a divalent group having the same structure as the $C_2$-$C_{60}$ alkynyl group.

A $C_3$-$C_{10}$ cycloalkyl group as used herein refers to a monovalent hydrocarbon monocyclic group having 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as the $C_3$-$C_{10}$ cycloalkyl group.

A $C_1$-$C_{10}$ heterocycloalkyl group as used herein refers to a monovalent monocyclic group having at least one hetero atom selected from N, O, P, and S as a ring-forming atom and 1 to 10 carbon atoms. Detailed examples thereof are a tetrahydrofuranyl group, and a tetrahydrothiophenyl group. A $C_1$-$C_{10}$ heterocycloalkylene group as used herein refers to a divalent group having the same structure as the $C_1$-$C_{10}$ heterocycloalkyl group.

A $C_3$-$C_{10}$ cycloalkenyl group as used herein refers to a monovalent monocyclic group that has 3 to 10 carbon atoms and at least one double bond in the ring thereof and which is not aromatic. Detailed examples thereof are a cyclopentenyl group, a cyclohexenyl group, and a cycloheptenyl group. A $C_3$-$C_{10}$ cycloalkenylene group as used herein refers to a divalent group having the same structure as the $C_3$-$C_{10}$ cycloalkenyl group.

A $C_1$-$C_{10}$ heterocycloalkenyl group as used herein refers to a monovalent monocyclic group that has at least one hetero atom selected from N, O, P, and S as a ring-forming atom, 1 to 10 carbon atoms, and at least one double bond in its ring. Detailed examples of the $C_2$-$C_{10}$ heterocycloalkenyl group are a 2,3-dihydrofuranyl group and a 2,3-dihydrothiophenyl group. A $C_1$-$C_{10}$ heterocycloalkenylene group as used herein refers to a divalent group having the same structure as the $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group as used herein refers to a monovalent group having a carbocyclic aromatic system that has at least one hetero atom selected from N, O, P, and S as a ring-forming atom, and 1 to 60 carbon atoms. A $C_1$-$C_{60}$ heteroarylene group as used herein refers to a divalent group having a carbocyclic aromatic system that has at least one hetero atom selected from N, O, P, and S as a ring-forming atom, and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group as used herein indicates —$OA_{102}$ (wherein $A_{102}$ is the $C_6$-$C_{60}$ aryl group), a $C_6$-$C_{60}$ arylthio group as used herein indicates —$SA_{103}$ (wherein $A_{103}$ is the $C_6$-$C_{60}$ aryl group), and a $C_7$-$C_{60}$ arylalkyl as used herein indicates -$A_{104}A_{105}$ (wherein $A_{105}$ is the $C_6$-$C_{60}$ aryl group and $A_{104}$ is the $C_1$-$C_{60}$ alkyl group).

A $C_2$-$C_{60}$ heteroaryloxy as used herein indicates —$OA_{106}$ (wherein $A_{106}$ is the $C_2$-$C_{60}$ heteroaryl group), a $C_2$-$C_{60}$ heteroarylthio indicates —$SA_{107}$ (wherein $A_{107}$ is the $C_2$-$C_{60}$ heteroaryl group), and a $C_3$-$C_{60}$ heteroarylalkyl indicates -$A_{108}A_{109}$ (wherein $A_{109}$ is the $C_2$-$C_{60}$ heteroaryl group and $A_{108}$ is the $C_1$-$C_{60}$ alkyl group).

At least one of substituents of the substituted $C_3$-$C_{60}$ cycloalkylene group, substituted $C_1$-$C_{60}$ heterocycloalkylene group, substituted $C_3$-$C_{60}$ cycloalkenylene group, substituted $C_1$-$C_{60}$ heterocycloalkenylene group, substituted $C_6$-$C_{60}$ arylene group, substituted $C_1$-$C_{60}$ heteroarylene group, substituted a divalent non-aromatic condensed polycyclic group, substituted a divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{60}$ cycloalkyl group, substituted $C_1$-$C_{10}$ heterocycloalkyl group, substituted $C_3$-$C_{60}$ cycloalkenyl group, substituted $C_1$-$C_{60}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_2$-$C_{60}$ heteroaryloxy group, substituted $C_2$-$C_{60}$ heteroarylthio group, and substituted $C_3$-$C_{60}$ heteroarylalkyl group as used herein may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, and —$Si(Q_{31})(Q_{32})(Q_{33})$, wherein $Q_1$ to $Q_3$, $Q_{11}$ to $Q_{13}$, $Q_{21}$ to $Q_{23}$, and $Q_{31}$ to $Q_{33}$ may be each independently selected from a hydrogen, a $C_1$-$C_{60}$ alkyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, and a $C_1$-$C_{60}$ heteroaryl group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{30}$ alkyl" refers to a $C_1$-$C_{30}$ alkyl group substituted with $C_6$-$C_{30}$ aryl group, the total number of carbon atoms in the resulting aryl substituted alkyl group is $C_7$-$C_{60}$.

The "biphenyl group" as used herein refers to "a phenyl group substituted with a phenyl group."

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that an amount of A used was identical to an amount of B used, in terms of a molar equivalent.

EXAMPLES

Synthesis of Compound 25

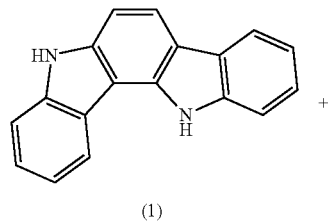

(1)

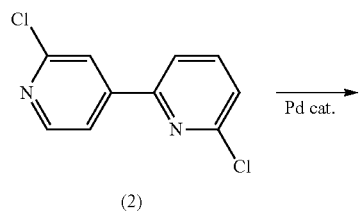

(2)

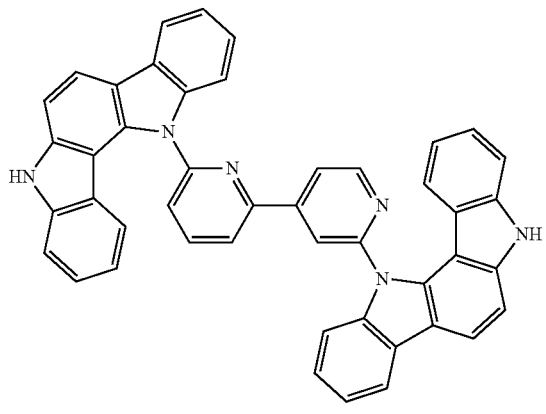

(3)

A mixture of 5,12-dihydroindolo[3,2-a]carbazole (1) (5.0 g, 19.51 mmol, available from FluoroChem, Ltd.), 2',6-dichloro-2,4'-bipyridine (2) (1.76 g, 7.80 mmol), and sodium-tert-butoxide (3.75 g, 39.02 mmol) in xylene (95 mL) was added and stirred at 165° C. under nitrogen for 12 h. To the reaction mixture was slowly added a solution of Pd(dba)$_2$ (0.90 g, 0.98 mmol), and tri-tert-butylphosphine (0.39 g, 1.95 mmol) in 15 mL of xylene. After allowing it to cool to room temperature, the reaction mixture was diluted with MeOH (200 mL) and filtered. The reaction mixture was carefully washed with water/MeOH (100/100 mL). The resulting brown solid was collected by filtration. The crude product was purified by column chromatography using dichloromethane/n-hexane (1/3) as eluent. The yellow solid was obtained then the product was recrystallized from toluene and finally dried under vacuum to give 12,12'-([2,4'-bipyridine]-2',6-diyl)bis(5,12-dihydroindolo[3,2-a]carbazole) (3) as a yellow crystal in 9.75 g (75%) yield.

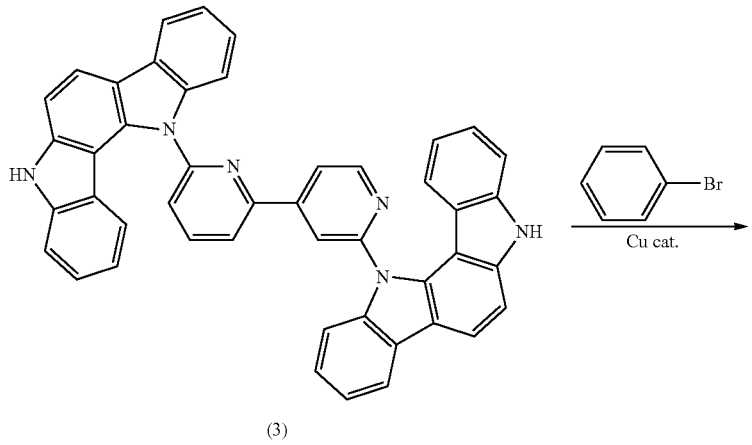

(3)

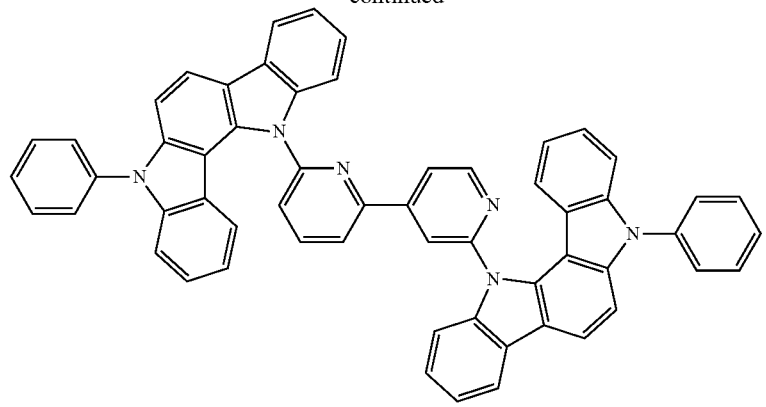

Compound 25

A mixture of 12,12'-([2,4'-bipyridine]-2',6-diyl)bis(5,12-dihydroindolo[3,2-a]carbazole) (3) (4.00 g, 6.02 mmol), bromobenzene (0.945 g, 6.02 mmol), CuI (0.03 g, 0.3 mmol), trans-1,2-diaminocyclohexane (0.137 g, 1.20 mmol), and potassium phosphate (1.92 g, 9.03 mmol) in dioxane (30 mL) was stirred at 110° C. for 12 h. After allowing it to cool to room temperature, the reaction mixture was diluted with toluene (500 mL) and filtered with celite. The reaction mixture was evaporated and the crude product was purified by column chromatography on silica gel using dichloromethane/n-hexane (1/9) as eluent. The yellow solid obtained after evaporating the solvent was recrystallized from toluene and finally dried under vacuum to give 5-phenyl-5,12-dihydroindolo[3,2-a]carbazole as a pale yellow powder in 2.15 g (41%) yield.

$^1$H NMR (500 MHz, CD$_2$Cl$_2$): δ (ppm) 8.87-8.85 (d, 1H), 8.21-8.12 (m, 5H), 8.08-8.06 (d, 1H), 8.02-7.99 (t, 1H), 7.85-7.84 (d, 1H), 7.68-7.60 (m, 8H), 7.56-7.53 (m, 5H), 7.39-7.19 (m, 10H), 6.87-6.83 (t, 1H), 6.80-6.77 (t, 1H), 6.17-6.13 (t, 2H); $^{13}$C NMR (500 MHz, CD$_2$Cl$_2$): δ (ppm) 154.5, 153.7, 151.01, 142.3, 141.8, 141.6, 141.2, 140.6, 138.1, 135.8, 130.5, 128.5, 126.2, 125.9, 125.3, 123.6, 122.4, 121.9, 121.6, 120.7, 120.0, 119.9, 118.8, 111.5, 109.9, 109.2, 105.5, 105.2; MALDI-TOF/MS: 820 [(M+H)$^+$].

Synthesis of Compound 2

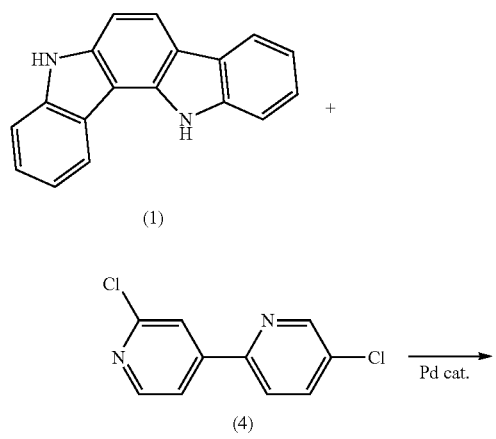

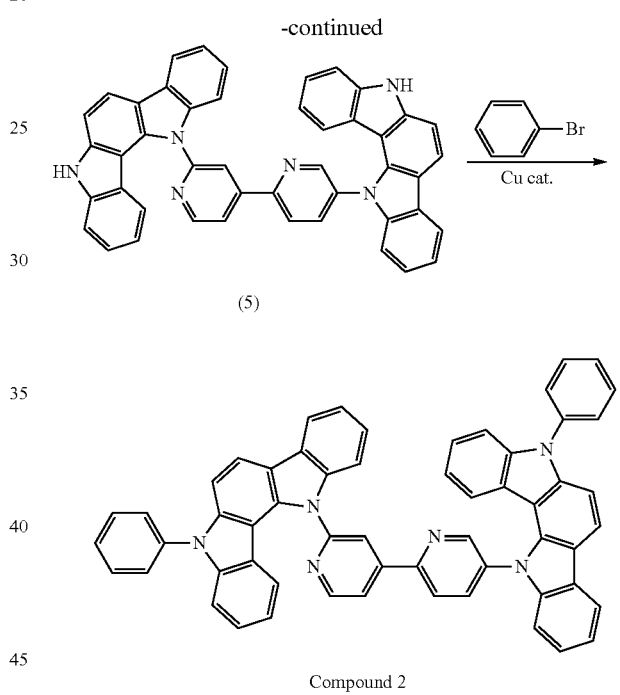

12,12'-([2,4'-bipyridine]-2',5-diyl)bis(5-phenyl-5,12-dihydroindolo[3,2-a]carbazole) (Compound 2) was obtained as pale yellow crystal (5.5 g, 90%) using a procedure analogous to that used for Compound 25, except that 2',5-dichloro-2,4'-bipyridine (4) was used instead of 2',6-dichloro-2,4'-bipyridine (2) to prepare 12,12'-([2,4'-bipyridine]-2',5-diyl)bis(5-phenyl-5,12-dihydroindolo[3,2-a]carbazole) (5).

$^1$H NMR (500 MHz, CD$_2$Cl$_2$): δ (ppm) 9.01-8.99 (d, 2H), 8.31-8.30 (d, 1H), 8.22-8.13 (m, 5H), 7.98-7.96 (dd, 1H), 7.92-7.88 (t, 2H), 7.68-7.63 (m, 6H), 7.59-7.55 (m, 4H), 7.44-7.37 (m, 8H), 7.36-7.34 (m, 2H), 7.29-7.17 (t, 1H), 6.99-6.87 (t, 1H), 6.55-6.49 (t, 1H), 6.31-6.29 (d, 1H), 6.03-6.01 (d, 1H); $^{13}$C NMR (500 MHz, CD$_2$Cl$_2$): δ (ppm) 154.7, 153.5, 151.1, 149.3, 142.4, 142.0, 141.2, 138.2, 136.9, 136.1, 130.5, 128.6, 126.0, 125.7, 125.2, 123.5, 122.4, 122.0, 121.9, 121.2, 120.8, 120.0, 119.9, 119.0, 118.5, 111.8, 110.1, 110.0, 109.1, 108.2, 105.2; MALDI-TOF/MS: 820 [(M+H)$^+$].

Example 1. Fabrication of OLED Containing Compound 25

A glass substrate with a 1500 Å-thick ITO (Indium tin oxide) electrode (first electrode, anode) formed thereon was washed with distilled water and ultrasonic waves. When the washing with distilled water was completed, sonicated washing was performed using a solvent, such as iso-propyl alcohol, acetone, or methanol. The resultant was dried and transferred to a plasma washer, and the resultant substrate was washed with oxygen plasma for 5 minutes and transferred to a vacuum depositor.

Compound HT3 was vacuum-deposited on the ITO electrode on the glass substrate to form a first hole injection layer having a thickness of 100 Å, Compound HT-D1 was vacuum-deposited on the first hole injection layer to form a second hole injection layer having a thickness of 100 Å, and mCP was deposited on the second hole injection layer to form an electron blocking layer having a thickness of 100 Å, thereby completing the manufacture of a hole transport region.

Compound 25 (dopant, 15 wt %) and mCP (host) were co-deposited on the hole transport region to form an emission layer having a thickness of 400 Å.

Compound ET3 was vacuum-deposited on the emission layer to form an electron transport layer having a thickness of 300 Å, ET-D1(Liq) was deposited on the electron transport layer to form an electron injection layer having a thickness of 10 Å, and an Al second electrode (cathode) having a thickness of 1,200 Å was formed on the electron injection layer, thereby completing the manufacture of an organic light-emitting device.

Example 2. Fabrication of OLED Containing Compound 2

The OLED containing Compound 2 was fabricated according to the procedure described in Example 1 above.

Evaluation Example 1: Singlet (S1) Energy Level, Triplet (T1) Energy Level, and $\Delta E_{ST}$ Evaluation Singlet (S1), and triplet (T1) energy levels of Compounds 2 and 25 were evaluated according to Table 2.

Evaluation Example 2: Photoluminescence Quantum Yield Evaluation

A sample was prepared by vacuum-depositing each of Compounds 25 and 2 as a dopant (15 percent by weight, wt %) on a quartz cell at a thickness of 100 Angstroms (Å) with DPEPO or mCBP-CN (a host). The sample was excited by excitation light having a wavelength of 340 nanometers (nm) in a nitrogen atmosphere by using C9920-02 and PMA-11 available from Hamamatsu Photonics, and thus a photoluminescence (PL) quantum yield of the sample was measured. The results are shown in Tables 3 to 8.

TABLE 3

| 15 wt % doped | PLQY | PL peak (nm) | Tau (μs) | DF-portion (%) | IQE (%) |
|---|---|---|---|---|---|
| DPEPO: Compound 25 | 0.249 | 483 | 8.38 | 93.0 | 23.9 |
| DPEPO: Compound 2 | 0.495 | 485 | 26.6 | 94.8 | 48.5 |
| mCBP-CN: Compound 25 | 0.163 | 486 | 3.401 | 74.0 | 13.5 |
| mCBP-CN: Compound 2 | 0.321 | 485 | 17.69 | 88.4 | 30.5 |

TABLE 4

| EL data | $EQE_{max}$ (%) | EL (nm) | Cd/A | $CIE_x$ | $CIE_y$ |
|---|---|---|---|---|---|
| DPEPO: Compound 25 | 9.2 | 486 | 21.5 | 0.215 | 0.343 |
| DPEPO: Compound 2 | 16.4 | 479 | 37.8 | 0.217 | 0.342 |

TABLE 5

| Compound | $E_q$ | S1 (max) | T1 (max) | ΔEST (onset) | S1 (onset) | T1 (onset) | PLQY (without $N_2$) | PLQY (with $N_2$) |
|---|---|---|---|---|---|---|---|---|
| 25 | 3.1 | 2.55 | 2.70 | 0 | 2.95 | 2.95 | 0.04 | 0.17 |
| 2 | 3.1 | 2.56 | 2.70 | 0.15 | 2.95 | 2.80 | 0.05 | 0.15 |

TABLE 2

| | |
|---|---|
| S1 energy level evaluation method | Photoluminescence spectrum of a mixture including toluene and each of the compounds (diluted at a concentration of $1 \times 10^{-4}$M) was measured by using a photoluminescence measuring device at room temperature, and peaks obtained therefrom were analyzed to calculate an S1 energy level. |
| T1 energy level evaluation method | Photoluminescence spectrum of a mixture including toluene and each of the compounds (diluted at a concentration of $1 \times 10^{-4}$M) in a quartz cell in liquid nitrogen (at 77 Kelvin, K) was measured by using a photoluminescence measuring device, and peaks that were only obtained at a low temperature compared to the general room temperature photoluminescence spectrum were analyzed to calculate a T1 energy level. |
| $\Delta E_{ST}$ | A gap between an S1 energy level and a T1 energy level was calculated. |

TABLE 6

| Device Data | $V_d$ | $C_d/A$ | $L_m/W$ | $C_d/m^2$ | $(CIE_x)$ | $(CIE_y)$ | $EQE_{max}$ (%) | EL (nm) |
|---|---|---|---|---|---|---|---|---|
| Comparative Compound | | | | | | | 10 | 515 |
| Compound 25 | 6.72 | 13.19 | 6.17 | 500 | 0.215 | 0.343 | 9.2 | 486 |
| Compound 2 | 6.44 | 14.28 | 6.97 | 500 | 0.217 | 0.342 | 16.4 | 479 |

Comparative Compound

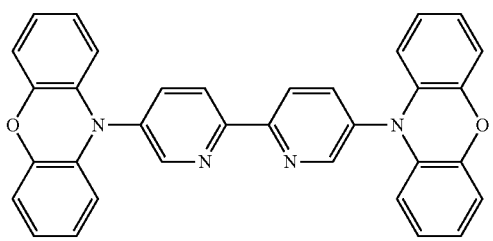 [SMILES: c1ccc2c(c1)Oc1ccccc1N2c1ccc(-c2ccc(N3c4ccccc4Oc4ccccc43)cn2)nc1]

Figure 2:
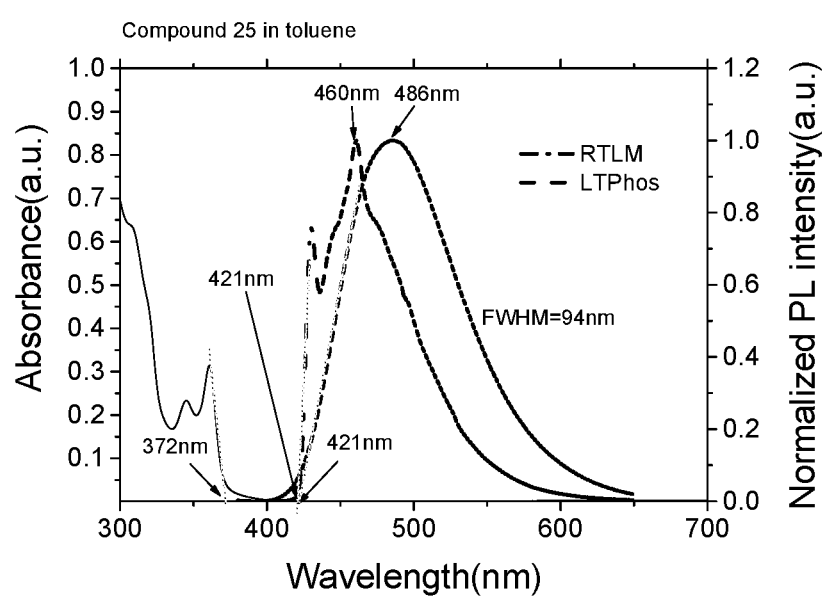
FIG. 2 is a graph of absorbance (arbitrary units, a. u.) and normalized intensity (arbitrary units, a. u.) versus wavelength (nanometers, nm) illustrating UV-vis absorption (Abs), room temperature (RT PL) and low temperature photoluminescence (LT PL) spectra of Compound 25.

As shown in FIG. 2, absorbance wavelength in UV-Vis was detected at 345 and 361 nm in toluene solvent for Compound 25. The maximum peak at 486 nm in toluene at room temperature was observed. At low temperature, 486 nm peak as phosphorescence spectrum was detected.

Figure 3:
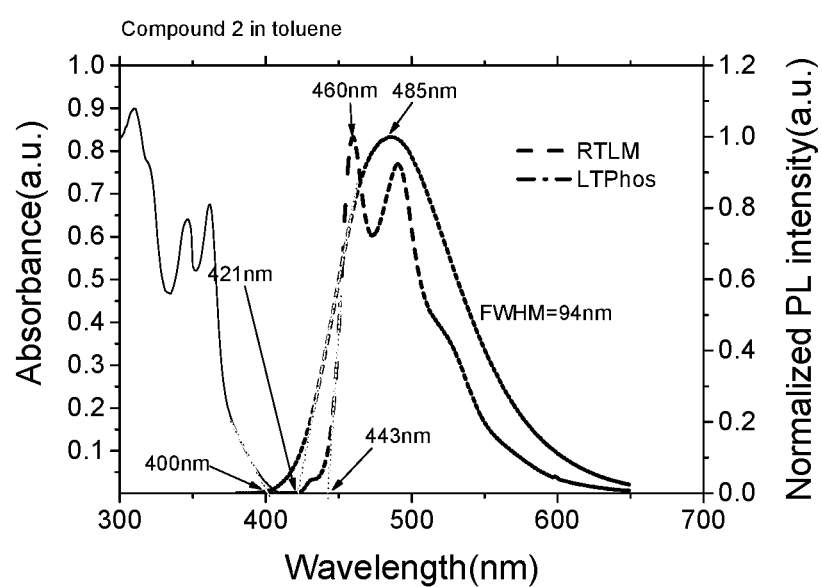
FIG. 3 is a graph of absorbance (arbitrary units, a. u.) and normalized intensity (arbitrary units, a. u.) versus wavelength (nanometers, nm) illustrating UV-vis absorption (Abs), room temperature (RT PL) and low temperature photoluminescence (LT PL) spectra of Compound 2.

As shown in FIG. 3, absorbance wavelength in UV-Vis was detected at 347 and 362 nm in toluene solvent for Compound 2. The maximum peak at 485 nm in toluene at room temperature was observed. At low temperature, 460 nm peak as phosphorescence spectrum was detected.

Figure 4:
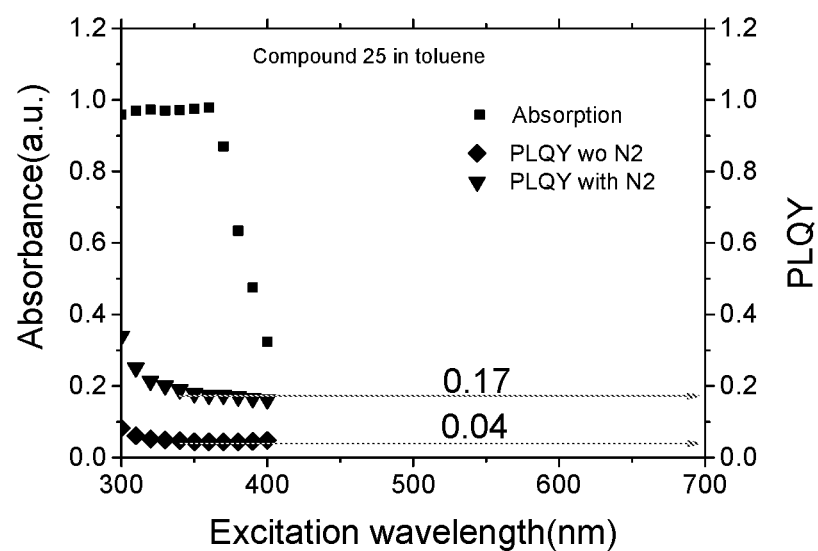
FIG. 4 is a graph of absorbance (arbitrary units, a. u.) and photoluminescence quantum yield (arbitrary units, a. u.) versus excitation wavelength (nanometers, nm) illustrating PLQY of Compound 25 in aerated (without $N_2$) and deoxygenated (with $N_2$) toluene solution.

As shown in FIG. 4, PLQY (photoluminescence quantum yield) of Compound 25 exhibited 0.04 in aerated toluene solution. In a deoxygenated toluene after bubbling with N2 gas, Compound 25 exhibited 0.17.

Figure 5:
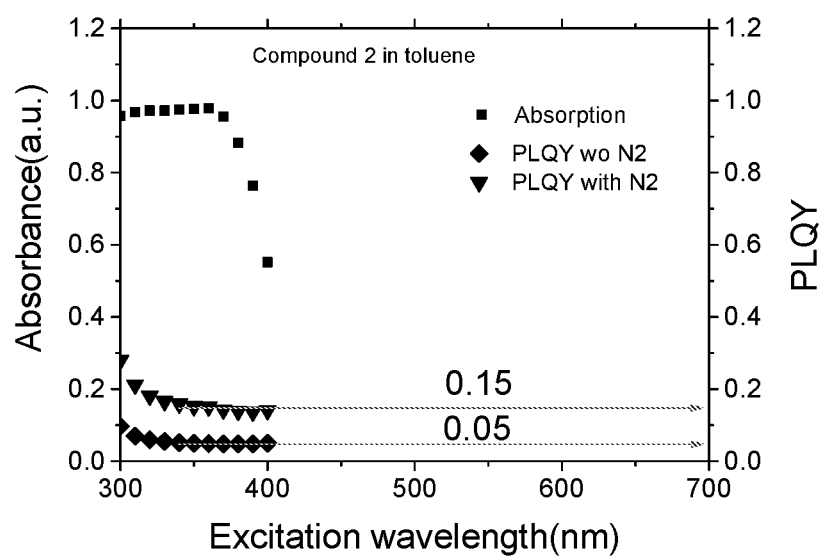
FIG. 5 is a graph of absorbance (arbitrary units, a. u.) and photoluminescence quantum yield (arbitrary units, a. u.) versus excitation wavelength (nanometers, nm) illustrating PLQY of Compound 2 in aerated (without $N_2$) and deoxygenated (with $N_2$) toluene solution.
Figure 6:
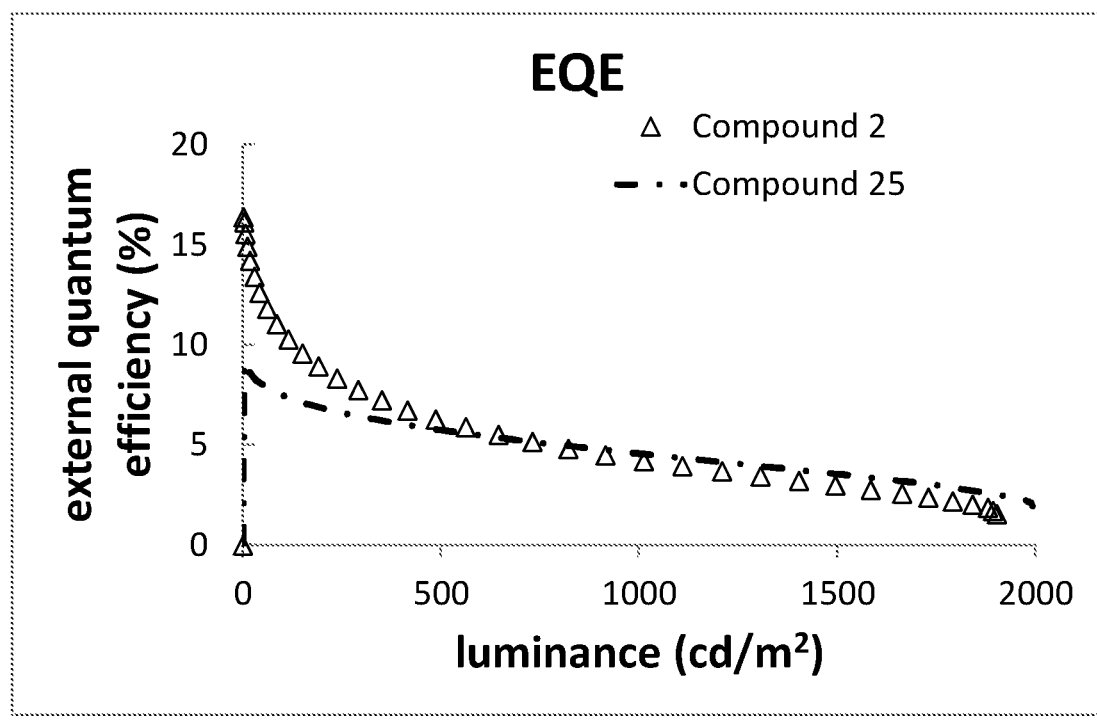
FIG. 6 is a graph of external quantum efficiency (EQE) (percent, %) versus luminance (candelas per square meter, $cd/m^2$) of Compounds 25 and 2.
Figure 7:
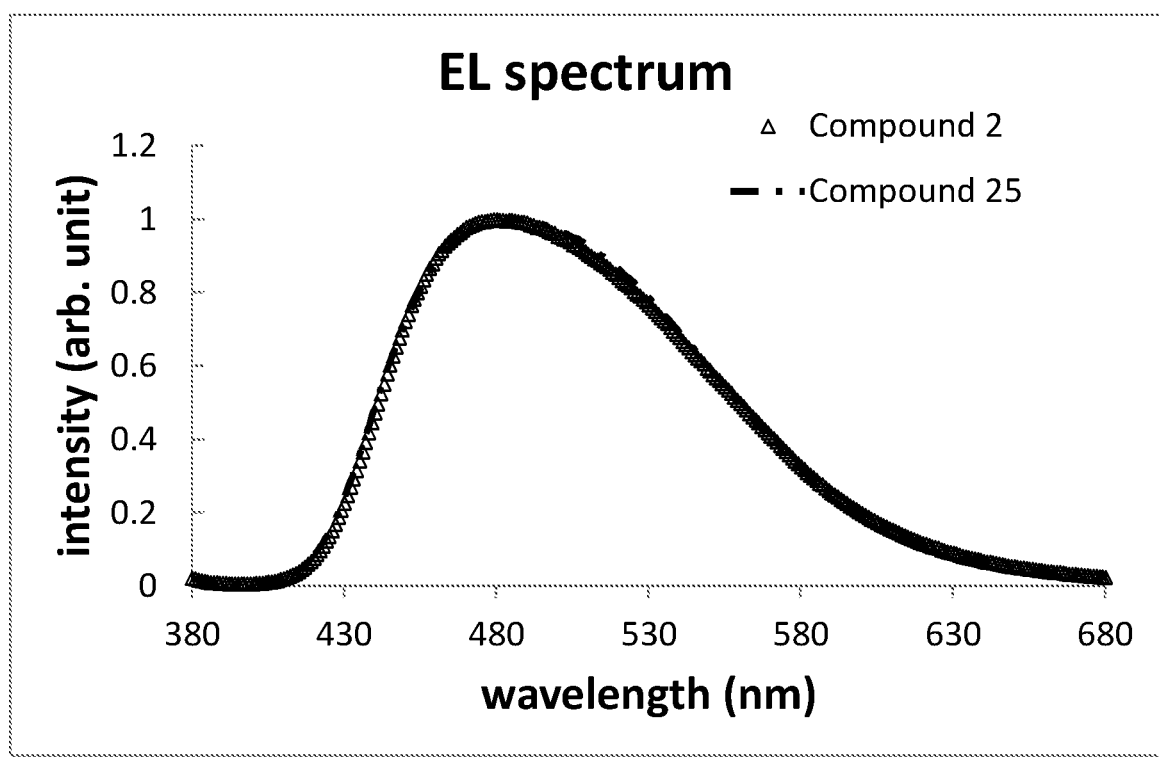
FIG. 7 is a graph of electroluminescence (EL) spectrum (arbitrary units, a. u.) versus wavelength (nanometers, nm) of Compounds 25 and 2.

As shown in FIG. 5, PLQY (photoluminescence quantum yield) of Compound 2 exhibited 0.05 in aerated toluene solution. In a deoxygenated toluene after bubbling with N2 gas, Compound 2 exhibited 0.15.

TABLE 7

| | | PL (nm) (energy level/eV) | | | PLQY (%) | | $\Delta E_{ST}$ (eV) | |
|---|---|---|---|---|---|---|---|---|
| | | RT | | LT | | | | |
| UV (nm) | On set | Peak top | On set | Peak top | w/o $N_2$ | $N_2$ | On set | Peak top |
| 400 | 421 (2.95) | 486 (2.55) | 421 (2.95) | 460 (2.70) | 4 | 17 | 0 | −0.15 |

TABLE 8

| | | PL (nm) (energy level/eV) | | | PLQY (%) | | $\Delta E_{ST}$ (eV) | |
|---|---|---|---|---|---|---|---|---|
| | | RT | | LT | | | | |
| UV (nm) | On set | Peak top | On set | Peak top | w/o $N_2$ | $N_2$ | On set | Peak top |
| 400 | 421 (2.95) | 485 (2.56) | 443 (2.80) | 460 (2.70) | 5 | 15 | 0.15 | −0.14 |

From the data shown in Table 3 to 8, it may be concluded that the compounds have electrooptical properties that are suitable as a material for an organic light-emitting device. Specifically, based on the results shown in Tables 3 to 8, it may be concluded that the organic light-emitting devices containing Compounds 2 and 25 had high efficiency and long lifespan compared to those characteristics of the organic light-emitting device of Comparative Example.

As described above, according to the one or more of the above embodiments, the organometallic compounds have excellent electrical properties and thermal stability and thus, an organic light-emitting device including the organometallic compounds may have a low driving voltage, high efficiency, high brightness, and a long lifespan.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:
1. A condensed cyclic compound represented by Formula 1:

Ar¹-(L₁)_{a1}-B-(L₂)_{a2}-Ar²     Formula 1 wherein, in Formula 1,
B is a group represented by Formula 2:

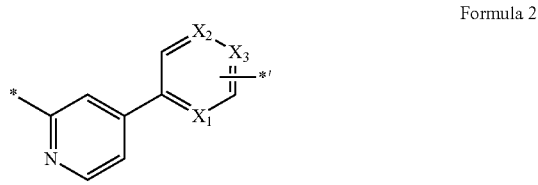

Formula 2 wherein, in Formula 2,
X₁ is N, X₂ is CH, and X₃ is CH;
X₁ is CH, X₂ is N, and X₃ is CH; or
X₁ is CH, X₂ is CH, and X₃ is N;
L₁ and L₂ are each independently selected from a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group,
wherein at least one of substituents of the substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_2$-$C_{60}$ heteroaryloxy group, substituted $C_2$-$C_{60}$ heteroarylthio group, and substituted $C_3$-$C_{60}$ heteroarylalkyl group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, and —Si($Q_1$)($Q_2$)($Q_3$), wherein $Q_1$ to $Q_3$ are each independently selected from a hydrogen, a $C_1$-$C_{60}$ alkyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, and a $C_1$-$C_{60}$ heteroaryl group;

* represents a point of connection to $Ar^1$ when a1 is 0;

* represents a point of connection to $L_1$ when a1 is 1 to 5;

*' represents a point of connection to $Ar^2$ when a2 is 0;

*' represents a point of connection to $L_2$ when a2 is 1 to 5;

a1 and a2 are each independently an integer selected from 0 to 5, provided that when a1 is 2 or greater, two or more groups $L_1$ are identical to or different from each other, and when a2 is 2 or greater, two or more groups $L_2$ are identical to or different from each other;

$Ar^1$ and $Ar^2$ are each independently a group represented by one of Formulae 3A to 3F

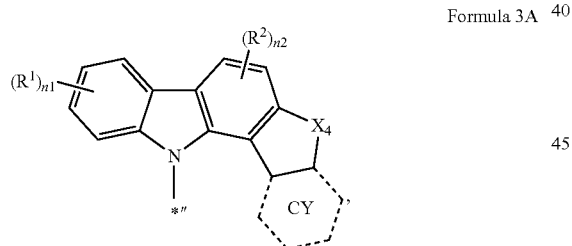

Formula 3A

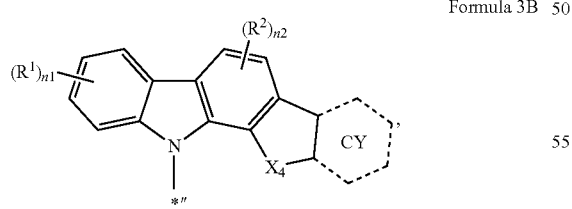

Formula 3B

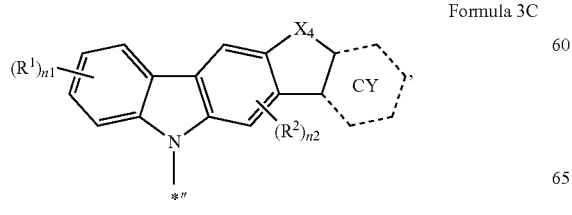

Formula 3C

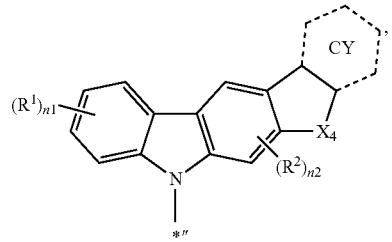

Formula 3D

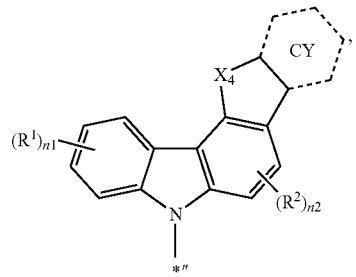

Formula 3E

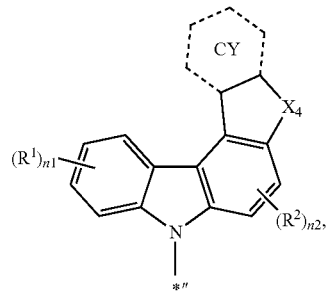

Formula 3F wherein, in Formulae 3A to 3F, $X_4$ is O, S, Se, N($R_3$), P(=O)($R_4$), C($R_5$)($R_6$), or Si($R_7$)($R_8$), provided that i) when $X_4$ is N($R_3$) then the sum of a1 and a2 is at least one, and ii) when $X_4$ is N($R_3$) and the sum of a1 and a2 is one, then $L_1$ and $L_2$ are not pyridinylene;

wherein, in Formulae 3A to 3F,

CY is a substituted or unsubstituted $C_6$-$C_{60}$ aryl ring or a substituted or unsubstituted $C_1$-$C_{60}$ heteroaryl ring, n1 is 0, 1, 2, or 4, n2 is 0 or 1, $R^1$, $R^2$, and $R^5$ to $R^8$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_1$-$C_{60}$ heterocycloalkyl group, a substituted or unsubstituted $C_3$-$C_{60}$ cycloalkenyl group, a substituted or unsubstituted $C_1$-$C_{60}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_7$-$C_{60}$ arylalkyl group, a substituted or unsubstituted $C_1$-$C_{60}$ heteroaryl group, a substituted or unsubstituted $C_2$-$C_{60}$ heteroaryloxy group, a substituted or unsubstituted $C_2$-$C_{60}$ heteroarylthio group, a substituted or unsubstituted $C_3$-$C_{60}$ heteroarylalkyl group, and —Si($Q_4$)($Q_5$)($Q_6$), wherein $Q_4$ to $Q_6$ are each independently selected from a hydrogen, a $C_1$-$C_{60}$ alkyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, and a $C_1$-$C_{60}$ heteroaryl group, $R^3$ and $R^4$ is a substituted or unsubstituted $C_6$-$C_{60}$ aryl group or a substituted or unsubstituted $C_1$-$C_{60}$ heteroaryl group, wherein at least one of substituents of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{60}$ heterocycloalkyl group, substituted $C_3$-$C_{60}$ cycloalkenyl group, substituted $C_1$-$C_{60}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_7$-$C_{60}$ arylalkyl group, substituted $C_1$-$C_{60}$ heteroaryl group, substituted $C_2$-$C_{60}$ heteroaryloxy group, substituted $C_2$-$C_{60}$ heteroarylthio group, and substituted $C_3$-$C_{60}$ heteroarylalkyl group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, a $C_6$-$C_{60}$ aryloxy group, a $C_6$-$C_{60}$ arylthio group, a $C_7$-$C_{60}$ arylalkyl group, a $C_1$-$C_{60}$ heteroaryl group, a $C_2$-$C_{60}$ heteroaryloxy group, a $C_2$-$C_{60}$ heteroarylthio group, a $C_3$-$C_{60}$ heteroarylalkyl group, and —Si($Q_7$)($Q_8$)($Q_9$), wherein $Q_7$ to $Q_9$ are each independently selected from a hydrogen, a $C_1$-$C_{60}$ alkyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, and a $C_1$-$C_{60}$ heteroaryl group, and

*" represents a point of connection of $Ar_1$ to B when a1 is 0,

*" represents a point of connection of $Ar_2$ to B when a2 is 0,

*" represents a point of connection of $Ar_1$ to $L_1$ when a1 is 1 to 5,

*" represents a point of connection to $Ar_2$ to $L_2$ when a2 is 1 to 5.

2. The condensed cyclic compound of claim 1, wherein, in Formula 1, $L_1$ and $L_2$ are each independently selected from a phenylene group, a pyridinylene group, a pyrimidinylene group, a pyrazinylene group, a pyridazinylene group, a triazinylene group, a dibenzofuranylene group, and a dibenzothiophenylene group; and a phenylene group, a pyridinylene group, a pyrimidinylene group, a pyrazinylene group, a pyridazinylene group, a triazinylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si($Q_{10}$)($Q_{11}$)($Q_{12}$), wherein $Q_{10}$ to $Q_{12}$ are each independently selected from a hydrogen, a $C_1$-$C_{60}$ alkyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, and a $C_1$-$C_{60}$ heteroaryl group.

3. The condensed cyclic compound of claim 1, wherein, in Formula 1, $L_1$ and $L_2$ are each independently selected from a phenylene group, a pyridinylene group, a pyrimidinylene group, and a triazinylene group; and a phenylene group, a pyridinylene group, a pyrimidinylene group, and a triazinylene group, each substituted with at least one selected from a deuterium, a methyl group, an ethyl group, an n-propyl group, an isopropyl group, an n-butyl group, an isobutyl group, a sec-butyl group, a tert-butyl group, a phenyl group, a pyridinyl group, a pyrimidinyl group, a pyrazinyl group, a pyridazinyl group, a triazinyl group, and —Si($Q_{10}$)($Q_{11}$)($Q_{12}$), wherein $Q_{10}$ to $Q_{12}$ are each independently selected from a hydrogen, a $C_1$-$C_{60}$ alkyl group, a $C_1$-$C_{60}$ alkoxy group, a $C_3$-$C_{60}$ cycloalkyl group, a $C_1$-$C_{60}$ heterocycloalkyl group, a $C_3$-$C_{60}$ cycloalkenyl group, a $C_1$-$C_{60}$ heterocycloalkenyl group, a $C_6$-$C_{60}$ aryl group, and a $C_1$-$C_{60}$ heteroaryl group.

4. The condensed cyclic compound of claim 1, wherein, in Formula 1, $L_1$ and $L_2$ are each independently selected from a phenylene group; and a phenylene group substituted with at least one selected from a deuterium, a methyl group, an ethyl group, an n-propyl group, an isopropyl group, an n-butyl group, an isobutyl group, a sec-butyl group, a tert-butyl group, a phenyl group, a pyridinyl group, a pyrimidinyl group, a pyrazinyl group, a pyridazinyl group, a triazinyl group, and —Si($Q_{10}$)($Q_{11}$)($Q_{12}$), wherein $Q_{10}$ to $Q_{12}$ are each independently selected from a hydrogen, a $C_1$-$C_{10}$ alkyl group, a $C_1$-$C_{10}$ alkoxy group, and a phenyl group.

5. The condensed cyclic compound of claim 1, wherein, in Formula 1, a1 is 0 and a2 is 0.

6. The condensed cyclic compound of claim 1, wherein, in Formulae 3A to 3F,

CY is an unsubstituted $C_6$-$C_{60}$ aryl ring.

7. The condensed cyclic compound of claim 1, wherein, in Formulae 2 and 3A to 3F, $R^1$, $R^2$, and $R^5$ to $R^8$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a C$_1$-C$_{20}$ alkyl group and a C$_1$-C$_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, a pyrimidinyl group, a pyrazinyl group, a pyridazinyl group, and a triazinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, and an imidazopyridinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, and an imidazopyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_2$-C$_{20}$ alkenyl group, a C$_2$-C$_{20}$ alkynyl group, a C$_1$-C$_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, and —Si(Q$_{13}$)(Q$_{14}$)(Q$_{15}$); and —Si(Q$_{16}$)(Q$_{17}$)(Q$_{18}$), wherein Q$_{13}$ to Q$_{15}$ and Q$_{16}$ to Q$_{18}$ are each independently selected from a hydrogen, a C$_1$-C$_{20}$ alkyl group, a C$_1$-C$_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cinnolinyl group, and a quinazolinyl group.

8. The condensed cyclic compound of claim 1, wherein, in Formulae 2 and 3A to 3F, R$^1$, R$^2$, and R$^5$ to R$^8$ are each independently selected from a hydrogen, a deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, and a C$_1$-C$_{10}$ alkoxy group;

a phenyl group, a naphthyl group, a pyridinyl group, a pyrimidinyl group, a pyrazinyl group, a pyridazinyl group, and a triazinyl group;

a phenyl group, a naphthyl group, a pyridinyl group, a pyrimidinyl group, a pyrazinyl group, a pyridazinyl group, and a triazinyl group, each substituted with at least one selected from a deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, a C$_1$-C$_{10}$ alkoxy group, a phenyl group, a naphthyl group, a pyridinyl group, a pyrimidinyl group, a pyrazinyl group, a pyridazinyl group, a triazinyl group, and —Si(Q$_{13}$)(Q$_{14}$)(Q$_{15}$); and —Si(Q$_{16}$)(Q$_{17}$)(Q$_{18}$), wherein Q$_{13}$ to Q$_{15}$ and Q$_{16}$ to Q$_{18}$ are each independently selected from a hydrogen, a C$_1$-C$_{10}$ alkyl group, a C$_1$-C$_{10}$ alkoxy group, a phenyl group, a naphthyl group, a pyridinyl group, a pyrimidinyl group, a pyrazinyl group, a pyridazinyl group, and a triazinyl group.

9. The condensed cyclic compound of claim 1, wherein, in Formulae 3A to 3F,

R$^3$ and R$^4$ are each a substituted or unsubstituted C$_6$-C$_{60}$ aryl group.

10. The condensed cyclic compound of claim 1, wherein, in Formulae 3A to 3F,

R$^3$ and R$^4$ are each a phenyl group; or a phenyl group substituted with at least one selected from a deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si($Q_{19}$)($Q_{20}$)($Q_{21}$), wherein $Q_{19}$ to $Q_{21}$ are each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group.

11. The condensed cyclic compound of claim 1, wherein, in Formulae 3A to 3F,
  $X_4$ is O, S, N($R_3$), and C($R_5$)($R_6$), $R_3$ is a phenyl group and $R_5$ and $R_6$ are each a methyl group.

12. The condensed cyclic compound of claim 1, wherein, in Formula 1,
  $Ar^1$ and $Ar^2$ are identical to each other.

13. The condensed cyclic compound of claim 1, wherein $Ar^1$ and $Ar^2$ are each independently selected from one of the following groups:

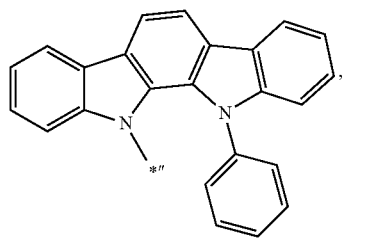

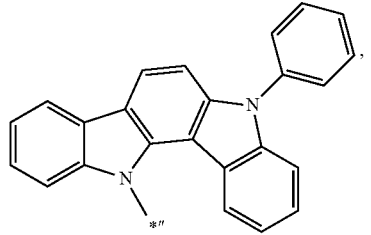

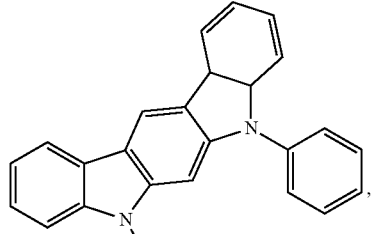

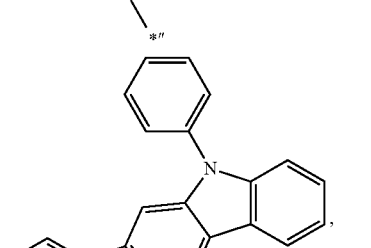

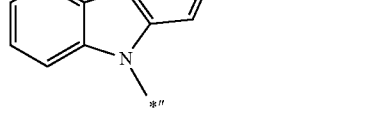

-continued

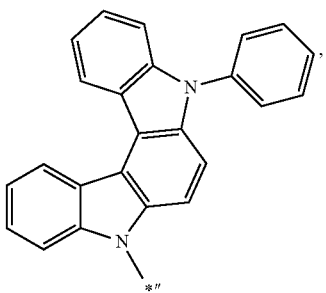

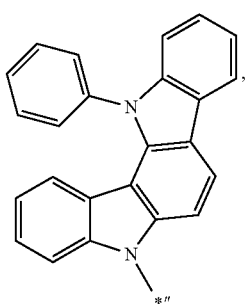

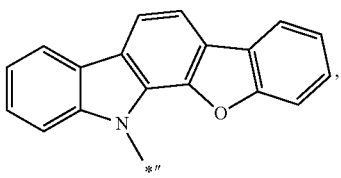

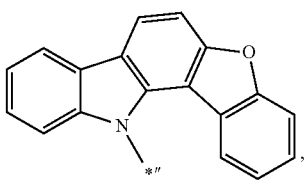

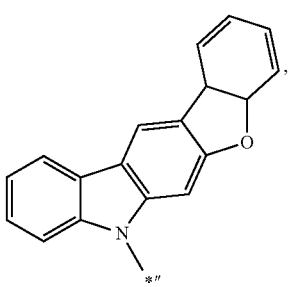

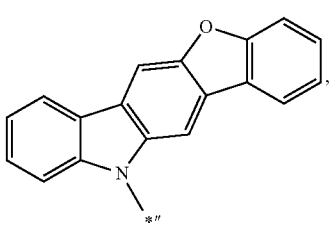

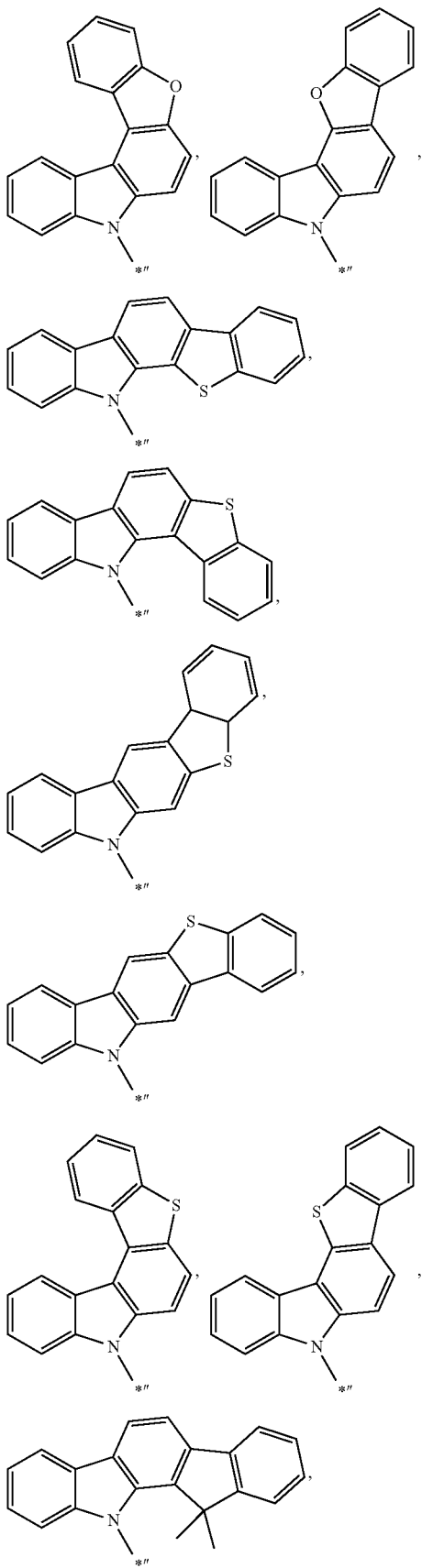
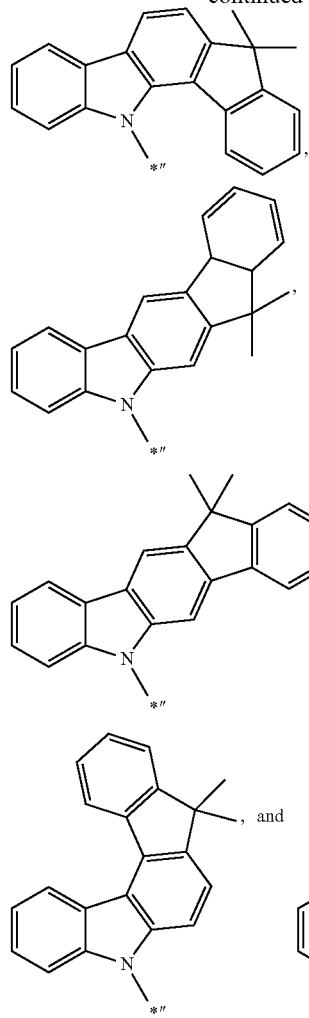

wherein, in the above groups,

*" represents a point of connection of Ar$_1$ to B when a1 is 0,

*" represents a point of connection of Ar$_2$ to B when a2 is 0,

*" represents a point of connection of Ar$_1$ to L$_1$ when a1 is 1 to 5,

*" represents a point of connection to Ar$_2$ to L$_2$ when a2 is 1 to 5.

14. An organic light-emitting device comprising:
a first electrode;
a second electrode; and
an organic layer disposed between the first electrode and the second electrode,
wherein the organic layer comprises an emission layer and at least one of the condensed cyclic compounds represented by Formula 1 of claim 1.

15. The organic light-emitting device of claim 14, wherein the first electrode is an anode,
the second electrode is a cathode, and
the organic layer comprises:
i) a hole transport region disposed between the first electrode and the emission layer, wherein the hole transport region comprises at least one selected from a hole injection layer, a hole transport layer, and an electron blocking layer; and ii) an electron transport region disposed between the emission layer and the second electrode, wherein the electron transport region comprises at least one selected from a hole blocking layer, an electron transport layer, and an electron injection layer.

16. The organic light-emitting device of claim 14, wherein the emission layer comprises the condensed cyclic compound represented by Formula 1.

17. The organic light-emitting device of claim 14, wherein the emission layer comprises the condensed cyclic compound represented by Formula 1 and a phosphorescent dopant, and
wherein an amount of the condensed cyclic compound is greater than an amount of the phosphorescent dopant.

18. The organic light-emitting device of claim 16, wherein the emission layer emits blue light.

19. The organic light-emitting device of claim 14, wherein the emission layer comprises the condensed cyclic compound represented by Formula 1, and
wherein the condensed cyclic compound represented by Formula 1 is a thermally activated delayed fluorescence emitter.

* * * * *